(12) United States Patent
Cattolico et al.

(10) Patent No.: US 10,738,297 B2
(45) Date of Patent: Aug. 11, 2020

(54) 3D PRINTABLE HYDROGEL MATERIALS

(71) Applicant: University of Washington, Seattle, WA (US)

(72) Inventors: Rose Ann Cattolico, Seattle, WA (US); Chloe Ramos Deodato, Seattle, WA (US); Alshakim Nelson, Seattle, WA (US); Robert Jun Ono, Seattle, WA (US); Abhijit Saha, Seattle, WA (US); Trevor Gerald Johnston, Washington, WA (US); Dylan Gary Karis, Seattle, WA (US)

(73) Assignee: University of Washington, Seattle, WA (US)

( * ) Notice: Subject to any disclaimer, the term of this patent is extended or adjusted under 35 U.S.C. 154(b) by 268 days.

(21) Appl. No.: 15/594,312

(22) Filed: May 12, 2017

(65) Prior Publication Data

US 2017/0327813 A1 Nov. 16, 2017

Related U.S. Application Data

(60) Provisional application No. 62/335,911, filed on May 13, 2016.

(51) Int. Cl.

| | | |
|---|---|---|
| C12N 11/04 | (2006.01) | |
| C08G 65/26 | (2006.01) | |
| C12N 11/08 | (2020.01) | |
| C08G 65/333 | (2006.01) | |
| B33Y 80/00 | (2015.01) | |
| B33Y 10/00 | (2015.01) | |
| B33Y 70/00 | (2020.01) | |
| C08G 65/30 | (2006.01) | |
| B29K 105/00 | (2006.01) | |
| C12P 7/06 | (2006.01) | |

(52) U.S. Cl.
CPC .............. *C12N 11/04* (2013.01); *B33Y 10/00* (2014.12); *B33Y 70/00* (2014.12); *B33Y 80/00* (2014.12); *C08G 65/2609* (2013.01); *C08G 65/2615* (2013.01); *C08G 65/30* (2013.01); *C08G 65/33351* (2013.01); *C12N 11/08* (2013.01); *C12P 7/06* (2013.01); *B29K 2105/0061* (2013.01); *C08G 2210/00* (2013.01); *C08G 2650/04* (2013.01); *C08G 2650/20* (2013.01); *C08G 2650/38* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 6,977,167 B2 | 12/2005 | Barclay | |
| 7,247,692 B2 * | 7/2007 | Laredo | .................. A61L 27/18 |
| | | | 351/159.33 |
| 7,999,023 B2 | 8/2011 | Menon et al. | |
| 9,278,465 B1 | 3/2016 | Worsley et al. | |
| 9,517,128 B2 | 12/2016 | McAlpine et al. | |
| 9,868,870 B2 * | 1/2018 | Engler | ................. C09D 11/102 |
| 2009/0239302 A1 | 9/2009 | Decher et al. | |
| 2011/0212501 A1 | 9/2011 | Yoo | |
| 2013/0164339 A1 | 6/2013 | Murphy et al. | |
| 2013/0190210 A1 | 7/2013 | Murphy et al. | |
| 2014/0243428 A1 | 8/2014 | Varghese et al. | |
| 2014/0257518 A1 | 9/2014 | McAlpine | |
| 2015/0030681 A1 | 1/2015 | Merry et al. | |
| 2016/0279868 A1 | 9/2016 | Burdick et al. | |
| 2017/0217091 A1 | 8/2017 | Hull | |
| 2017/0281828 A1 | 10/2017 | Zhang et al. | |
| 2018/0002658 A1 | 1/2018 | Miller et al. | |

FOREIGN PATENT DOCUMENTS

| | | |
|---|---|---|
| CN | 103977453 A1 | 8/2014 |
| WO | 2015/173020 A1 | 11/2015 |
| WO | 2017/045080 | 3/2017 |

OTHER PUBLICATIONS

Aebersold et al., "Mass spectrometry-based proteomics" Nature 422: 198-207 (2003).
Bagert et al., "Quantitative, time-resolved proteomic analysis by combining bioorthogonal noncanonical amino acid tagging and pulsed stable isotope labeling my amino acids in cell culture" Mol. Cell. Proteomics 13(5): 1352-1358 (2014).
Baskin et al., "Copper-free click chemistry for dynamic in vivo imaging" Proc Natl Acad Sci 104(43): 16793-16797 (2007).
Beatty, et al., "Live-cell imaging of cellular proteins by a strain-promoted azide-alkyne cycloaddition" ChemBioChem 11:2092-2095 (2010).
Brennan, et al., "Biofuels from microalgae—A review of technologies for production, processing, and extractions of biofuels and co-products" Renew. Sust. Energ. Rev. 14:557-577 (2010).
Bryant, et al., "Cytocompatibility of UV and visible light photoinitiating systems on cultured NIH/3T3 fibroblasts in vitro" J. Biomater. Sci. Polymer Edn 11(5): 439-457 (2000).
Cheetham, "Physical studies on the mechanical stability of columns of calcium alginate gel pellets containing entrapped microbial cells" Enzyme Microb. Technol. 1:183-188 (1979).
De-Bashan, et al., "Immobilized microalgae for removing pollutants: Review of practical aspects" Bioresour. Technol. 101: 1611-1627 (2010).
Deforest, et al., "A photoreversible protein-patterning approach for guiding stem cell fate in three-dimensional gels" Nat. Mat. 14: 523-531 (2015).

(Continued)

*Primary Examiner* — Jeffrey T. Palenik
(74) *Attorney, Agent, or Firm* — McDonnell Boehnen Hulbert & Berghoff LLP

(57) ABSTRACT

Hydrogel compositions including a polymer uniformly embedded with a loading agent are provided. Also provided are methods for extrusion printing hydrogel compositions to provide extruded hydrogel compositions, which can be crosslinked to provide crosslinked hydrogel structures. Also provided are methods for using crosslinked hydrogel structures in chemical processes.

17 Claims, 10 Drawing Sheets

(56) References Cited

OTHER PUBLICATIONS

Deforest, et al., "Sequential click reactions for synthesizing and patterning three-dimensional cell microenvironments" Nat. Mat. 8: 659-664 (2009).

Deforest, et al., "Cytocompatible click-based hydrogels with dynamically tunable properties through orthogonal photoconjugation and photocleavage reactions" 3: 925-931 (2011).

Dieterich, et al., "Labeling, detection and identification of newly synthesized proteomes with bioorthogonal non-canonical amino-acid tagging" Nat. Protoc. 2(3): 532-540 (2007).

Dieterich, et al., "In situ visualization and dynamics of newly synthesized proteins in rat hippocampal neurons" Nat. Neurosci. 13(7): 897-907 (2010).

Dieterich, et al., "Selective identification of newly synthesized proteins in mammalian cells using bioorthogonal noncanonical amino acid tagging (BONCAT)" Proc. Natl Acad. Sci. 103(25): 9482-9487.

Doelle, et al., "Zymomonas Mobilis—Science and industrial application" Crit. Rev. Biotechnol. 13(1): 57-98 (1993).

Dommerholt, et al., "Readily accessible bicyclononynes for bioorthogonal labeling and three-dimensional imaging of living cells" Angew. Chem. Int. Ed. 49: 9422-9425 (2010).

Domon, et al., "Mass spectrometry and protein analysis" Science 312: 212-217 (2006).

Duan, et al., "3D Bioprinting of heterogenous aortic valve conduits with alginate/gelatin hydrogels" J. Biomed. Mater. Res. A 101A(5): 1255-1264 (2012).

Freeman, et al., "Immobilization of microbial cells in crosslinked, prepolymerized, linear polyacrylamide gels: antibiotic production by immobilized *Streptomyces clavuligerus* cells" Biotechnol. Bioeng. 13: 2747-2759 (1981).

Ghaffar, et al., "Recent trends in lactic acid biotechnology: A brief review on production to purification" J. Radiat. Res. Appl. Sci. 7: 222-229 (2014).

Herrick, "Introduction to Industrial Fermentation" Ind. Eng. Chem. 22(11): 1148 (1930).

Hong, et al., "3D printing of highly stretchable and tough hydrogels into complex, cellularized structures" Adv. Mater. 27: 4035-4040 (2015).

Howden, et al., "QuaNCAT: quantitating proteome dynamics in primary cells" Nat. Methods 10(4): 343-346 (2013).

Huang, et al., "A novel magnetic triple-responsive composite semi-IPN hydrogels for targeted and controlled drug delivery" Eur. Polym. J. 48: 1734-1744 (2012).

Kiick et al., "Incorporation of azides into recombinant proteins for chemoselective modification by the Staudinger igation" Proc. Natl Acad. Sci. 99(1) 19-24.

Larance, et al., "Multidimensional proteomics for cell biology" Nat. Rev. 16: 269-280 (2015).

Lennox, et al., "Process monitoring of an industrial fed-batch fermentation" Biotechnol. Bioeng. 74(2): 125-135 (2001).

Lim, et al., "Visible light polymerized hydrogels with improved cell survival and metabolic activity" Front. Bioeng. Biotechnol. Conference abstract: 10th World Biomaterials Congress (2016).

Lozano, et al., "3D printing of layered brain-like structures using peptide modified gellan gum substrates" Biomater. 67: 264-273 (2015).

Margaritis, et al., "Advances in ethanol production using immobilized cell systems" CRC Grit. Rev. Biotechnol. 1(4): 339-393.

Mata, et al., "Microalgae for biodiesel production and other applications: A review" Renew. Sust. Energ. Rev. 14:217-232 (2010).

McGhee, et al., "Continuous and static fermentation of glucose to ethanol by immobilized *Saccharaomyces cerevisiae* cells of different ages" Appl. Env. Microbiol. 44(1): 19-22 (1982).

Moreno-Garrido, "Microalgae immobilization: Current techniques and uses" Bioresour. Technol. 99: 3949-3964 (2008).

Nagarajan, et al., "Uncoupling reproduction from metabolism extends chonological lifespan in yeast" Proc. Natl Acad. Sci. 111(15): 1538-1547 (2014).

Pandey, et al., "Proteomics to study genes and genomes" Nature 405: 837-846 (2000).

Pataky, et al., "Microdrop printing of hydrogel bioinks into 3D tissue-like geometries" 24: 391-396 (2012).

Gu, et al., "Three-dimensional bio-printing" Sci. China Life Sci. 58(5): 411-419 (2015).

Roth, et al., "A concise and scalable route to L-azidohomoalanine" Nat. Protoc. 5(12): 1967-1973 (2010).

Sivaraman, et al., "Continuous ethanol production by yeast cells immobilized in open pore gelatin matrix" Biotechnol. Let. 4(6): 359-364 (1982).

Sletten, et al., "Bioorthogonal chemistry: Fishing for selectivity in a sea of functionality" Angew. Chem. Int. Ed. 48: 6974-6998 (2009).

Spolaore, et al., "Commerical applications of microalgae" J. Biosci. Bioeng. 101(2): 87-96 (2006).

Szychowski, et al., "Cleavage biotin probes for labeling of biomolecules via azide-alkyne cycloaddition" J. Am. Chem. Soc. 132: 18351-18360 (2010).

Takata, et al., "Screening of matrix suitable for immobilization of microbial cells" J. Solid-Phase Biochem. 2(3): 225-236 (1977).

Taniguchi, et al., "Quantifying *E. coli* proteome and transcriptome with single-molecule sensitivity in single cells" Science 329: 533-538 (2010).

Thayer, "End-to-end chemistry" Chemical & Engineering News 92(21): 13-21 (2014).

Verbelen, et al., "Immobilized yeast cell systems for continuous fermentation applications" Biotechnol. Lett. 28:1515-1525 (2006).

Vogel, et al., "Insights into the regulation of protein abundance from proteomic and transcriptomic analyses" Nat. Rev. 13: 227-232 (2012).

Wong, et al., "Low-dose, long-wave UV light does not affect gene expression of human mesenchymal stem cells" PloS One 10(9): e0139307 (2015).

Zhang, et al., "Dual-responsive hydrogels for direct-write 3D printing" Macromol. 48: 6482-6488 (2015).

Zhu, et al., "Microalgal biofuels: Flexible bioenergies for sustainable development" Renew. Sust. Energ. Rev. 30: 1035-1046 (2014).

\* cited by examiner

3D PRINTABLE HYDROGEL MATERIALS

CROSS-REFERENCE TO RELATED APPLICATIONS

The present application claims priority to U.S. Provisional Patent Application No. 62/335,911, filed May 13, 2016, which is entirely incorporated by reference herein for all purposes.

BACKGROUND OF THE INVENTION

Field of the Invention

The present disclosure is generally directed to hydrogel materials, methods for printing hydrogel materials, and method for catalyzing chemical reactions using printed hydrogel materials.

Description of Related Art

Unless otherwise indicated herein, the materials described in this section are not prior art to the claims in this application and are not admitted to be prior art by inclusion in this section.

Algal, bacterial, or yeast culture is ubiquitous in the chemical and biotech industries for the large-scale production of food ingredients, metabolites, pharmaceuticals, biofuels, and chemical precursors for bioplastics. Product synthesis using a batch process, involves combining living organisms, metabolites, nutrients, and water in a large reactor. The efficiency of the generation of a desired product requires strict control over physical parameters and chemical reactant concentrations, in the reaction vessel, typically for several days. For example, fermentation is an exothermic process, but excessively temperatures can be detrimental to the microbes used in the reaction. Likewise, the concentration levels of fermentation products can also be toxic to the cells (e.g., ethanol).

Because of the inefficiencies of batch processes, continuous processes, in which the reactants flow through a reactor system where the reaction takes place, and the desired product flows out of the reactor system, would be generally preferred in the commercial production of a desired product. A hydrogel structure containing an entrapped cell capable of catalyzing chemical reactions would be useful in a continuous culture process for the production of chemical species.

SUMMARY

Hydrogel compositions that are responsive to temperature, applied pressure (shear thinning) and chemical crosslinking are presented. Because of these properties, the hydrogel compositions can be uniformly embedded with a loading agent, extrusion ("3D") printed, and crosslinked. The resulting crosslinked hydrogel structures do not chemically or physically degrade in water under ambient conditions, and can therefore be used in various chemical processes involving the loading agent.

In one aspect, the invention provides a polymer having the structure of Formula (I):

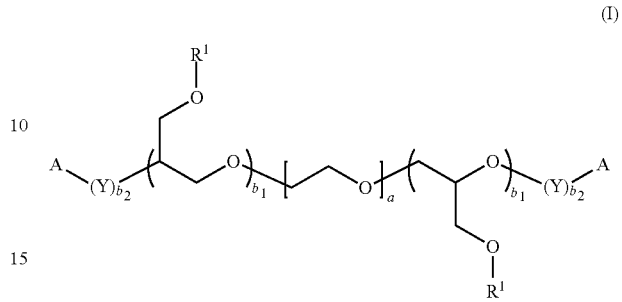

wherein a is selected to provide a poly(ethylene glycol) block polymer with an $M_n$ of about 500 to about 100,000;

$R^1$ is $C_{1-12}$alkyl, $C_{1-12}$alkyl-OR or $C_{1-12}$alkyl-NR$_2$, wherein each R is independently hydrogen or $C_{1-12}$alkyl;

$(Y)_{b2}$ is absent or a glycidyl ether derivative of the structure:

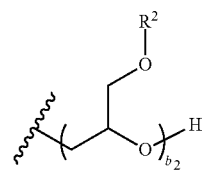

wherein $R^2$ is $C_{1-12}$alkenyl;

each $b_1$ and $b_2$ are independently selected to provide a random glycidyl ether derived copolymer with an $M_n$ about 100 to about 30,000; and A is hydrogen or a (meth)acrylate derivative of the structure:

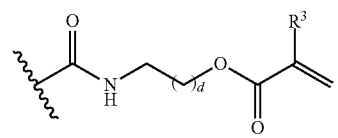

wherein $R^3$ is hydrogen or methyl; and d is 0, 1, 2, 3, 4, 5, 6, 7, 8, 9, 10, 11 or 12;

provided that (a) when $(Y)_{b2}$ is the glycidyl ether derivative, A is hydrogen; and (b) when (Y)b$_2$ is absent, A is the (meth)acrylate derivative.

In some embodiments, the polymer has the structure of Formula (II):

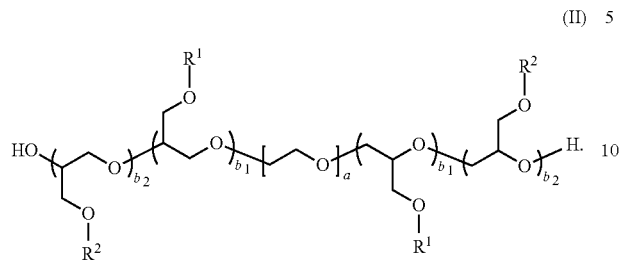

(II)

In some embodiments, the polymer has the structure of Formula (III):

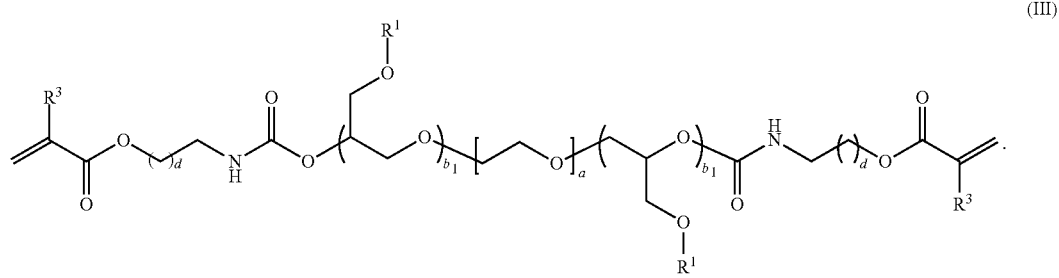

(III)

In another aspect, the disclosure provides a hydrogel composition including a polymer of Formula (I) and an aqueous medium.

In another aspect, the disclosure provides a crosslinked hydrogel structure including a polymer of Formula (I), an aqueous media, and a loading agent, wherein the polymer includes crosslinks derived from the alkene groups of $R^2$ in different polymer chains, or the polymer includes crosslinks derived from the alkene groups of the (meth)acrylate derivative in different polymer chains.

In another aspect, the disclosure provides a method for forming a crosslinked hydrogel structure. The method may involve subjecting a polymer composition including a polymer of Formula (I), an aqueous media, a photoinitiator and a loading agent to UV light, thereby initiating crosslinking between and the alkene groups of $R^2$ in different polymer chains, or between the alkene groups of the (meth)acrylate derivative in different polymer chains.

In another aspect, the disclosure provides a method for extrusion printing a polymer composition. The method may involve:

obtaining a hydrogel composition including a polymer of Formula (I), an aqueous media, a photoinitiator and a loading agent; and extrusion printing the composition to provide an extruded hydrogel composition.

In another aspect, the disclosure provides a method for performing a chemical reaction involving the loading agent. The method may involve:

subjecting a crosslinked hydrogel structure as described above to a reactant capable of undergoing chemical reaction; and recovering the product of the chemical reaction.

DETAILED DESCRIPTION

Figure 1:
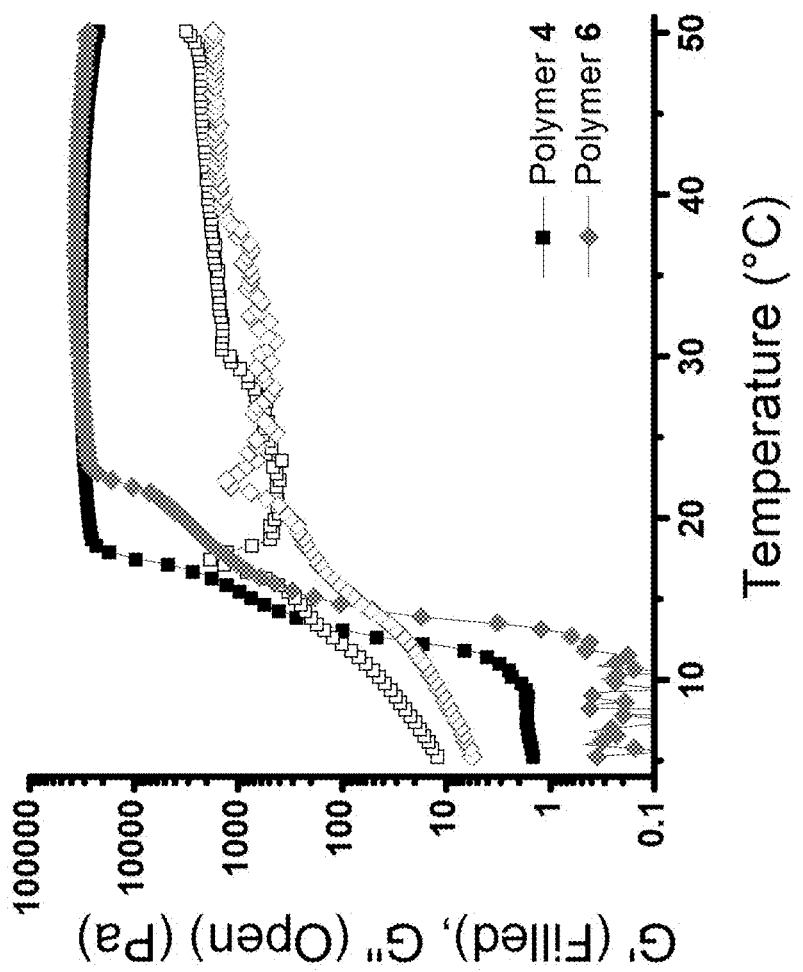
FIG. 1 is a dynamic oscillatory temperature ramp curve of 18 wt % polymer 4 (black) and 20 wt % polymer 6 (gray) hydrogels showing storage (filled) and loss (open) moduli, in accordance with an example embodiment.

The present disclosure relates to polymers, hydrogel materials, methods for printing hydrogel materials, and methods for catalyzing chemical reactions using printed hydrogel materials.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, isopropyl, butyl, isobutyl, sec-butyl, tert-butyl, pentyl, isopentyl, hexyl, etc. The alkyl group is typically monovalent, but can be divalent, such as when the alkyl group links two moieties together.

As used herein, the term "alkenyl" refers to either a straight chain or branched hydrocarbon of 2 to 6 carbon atoms, having at least one double bond. Examples of alkenyl groups include, but are not limited to, vinyl, allyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

In one aspect, the invention provides a polymer having the structure of Formula (I):

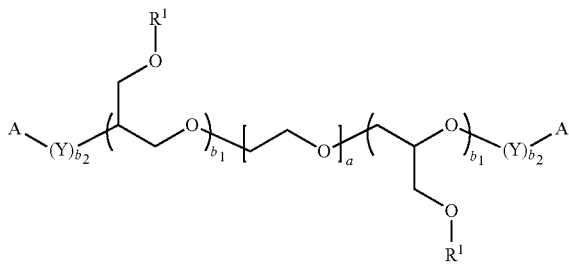

(I)

wherein a is selected to provide a poly(ethylene glycol) block polymer with an $M_n$ of about 500 to about 100,000;

$R^1$ is $C_{1-12}$alkyl, $C_{1-12}$alkyl-OR or $C_{1-12}$alkyl-$NR_2$, wherein each R is independently hydrogen or $C_{1-12}$alkyl;

$(Y)_{b2}$ is absent or a glycidyl ether derivative of the structure:

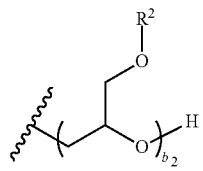

wherein $R^2$ is $C_{1-12}$alkenyl;

each $b_1$ and $b_2$ are independently selected to provide a random glycidyl ether derived copolymer with an $M_n$ about 100 to about 30,000; and A is hydrogen or a (meth)acrylate derivative of the structure:

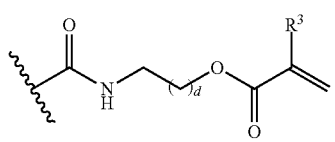

wherein $R^3$ is hydrogen or methyl; and d is 0, 1, 2, 3, 4, 5, 6, 7, 8, 9, 10, 11 or 12;

provided that (c) when $(Y)_{b2}$ is the glycidyl ether derivative, A is hydrogen; and (d) when $(Y)b_2$ is absent, A is the (meth)acrylate derivative.

In certain embodiments, a is selected so that the $M_n$ of the poly(ethylene glycol) block falls within a range listed in each row of Table 1.

TABLE 1

| $M_n$ range of the poly(ethylene glycol) block portion of the polymer (values are approximate). | |
|---|---|
| Low | High |
| 500 | 90,000 |
| 500 | 80,000 |
| 500 | 70,000 |
| 500 | 60,000 |
| 1,000 | 100,000 |
| 1,000 | 90,000 |
| 1,000 | 80,000 |
| 1,000 | 70,000 |
| 1,000 | 60,000 |
| 500 | 50,000 |
| 2500 | 48,000 |
| 4500 | 46,000 |
| 6500 | 44,000 |
| 8500 | 42,000 |
| 10500 | 40,000 |
| 12500 | 38,000 |
| 14500 | 36,000 |
| 16500 | 34,000 |
| 18500 | 32,000 |
| 20500 | 30,000 |
| 22500 | 28,000 |
| 24500 | 26,000 |
| 2500 | 26000 |
| 4500 | 28000 |
| 6500 | 30000 |
| 8500 | 32000 |
| 10500 | 34000 |
| 12500 | 36000 |
| 14500 | 38000 |
| 16500 | 40000 |
| 18500 | 42000 |
| 20500 | 44000 |
| 22500 | 46000 |
| 24500 | 48000 |

In some embodiments, a is selected to provide a poly(ethylene glycol) block with an $M_n$ about 5,000 to about 10,000.

In certain embodiments, b, $b_1$ and $b_2$ are selected so that the $M_n$ of the glycidyl ether derived copolymer block falls within a range listed in each row of Table 2.

TABLE 2

| $M_n$ range of the glycidyl ether derived copolymer block portion of the polymer (values are approximate) | |
|---|---|
| Low | High |
| 500 | 30,000 |
| 1,500 | 29,000 |
| 2,500 | 28,000 |
| 3,500 | 27,000 |
| 4,500 | 26,000 |
| 5,500 | 25,000 |
| 6,500 | 24,000 |
| 7,500 | 23,000 |

TABLE 2-continued

M_n range of the glycidyl ether derived copolymer
block portion of the polymer (values are approximate)

| Low | High |
|---|---|
| 8,500 | 22,000 |
| 9,500 | 21,000 |
| 10,500 | 20,000 |
| 11,500 | 19,000 |
| 12,500 | 18,000 |
| 13,500 | 17,000 |
| 14,500 | 16,000 |
| 1,500 | 16,000 |
| 2,500 | 17,000 |
| 3,500 | 18,000 |
| 4,500 | 19,000 |
| 5,500 | 20,000 |
| 6,500 | 21,000 |
| 7,500 | 22,000 |
| 8,500 | 23,000 |
| 9,500 | 24,000 |
| 10,500 | 25,000 |
| 11,500 | 26,000 |
| 12,500 | 27,000 |
| 13,500 | 28,000 |
| 14,500 | 29,000 |

In some embodiments, b, $b_1$ and $b_2$ are independently selected to provide a glycidyl ether derived copolymer block with an $M_n$ about 1,000 to about 10,000. In other embodiments, b, $b_1$ and $b_2$ are independently selected to provide a glycidyl ether derivative block with an $M_n$ about 1,000 to about 4,000.

In some embodiments, d is selected from one of the following groups (1a)-(1nn):

| | |
|---|---|
| (1a) 1, 2, 3, 4, 5, 6, 7, 8, 9, 10, 11 or 12 | (1b) 1, 2, 3, 4, 5, 6, 7, 8, 9 or 10 |
| (1c) 1, 2, 3, 4, 5, 6, 7 or 8 | (1d) 1, 2, 3, 4, 5 or 6 |
| (1e) 1, 2, 3, 4 or 5 | (1f) 1, 2, 3 or 4 |
| (1g) 1, 2 or 3 | (1h) 1 or 2 |
| (1i) 2, 3, 4, 5, 6, 7, 8, 9, 10, 11 or 12 | (1j) 2, 3, 4, 5, 6, 7, 8, 9 or 10 |
| (1k) 2, 3, 4, 5, 6, 7 or 8 | (1l) 2, 3, 4, 5 or 6 |
| (1m) 2, 3, 4 or 5 | (1n) 2, 3 or 4 |
| (1o) 2 or 3 | (1p) 3, 4, 5, 6, 7, 8, 9, 10, 11 or 12 |
| (1q) 3, 4, 5, 6, 7, 8, 9 or 10 | (1r) 3, 4, 5, 6, 7 or 8 |
| (1s) 3, 4, 5 or 6 | (1t) 3, 4 or 5 |
| (1u) 3 or 4 | (1v) 1, 3, 4, 5, 6, 7, 8, 9, 10, 11 or 12 |
| (1w) 1, 3, 4, 5, 6, 7, 8, 9 or 10 | (1x) 1, 3, 4, 5, 6, 7 or 8 |
| (1y) 1, 3, 4, 5 or 6 | (1z) 1, 3, 4 or 5 |
| (1aa) 1, 3 or 4 | (1bb) 1 or 3 |
| (1cc) 1 | (1dd) 2 |
| (1ee) 3 | (1ff) 4 |
| (1gg) 5 | (1hh) 6 |
| (1ii) 7 | (1jj) 8 |
| (1kk) 9 | (1ll) 10 |
| (1mm) 11 | (1nn) 12 |

In some embodiments, $R^1$ is $C_{1-6}$alkyl. In other embodiments, $R^1$ is $C_{1-5}$alkyl, $C_{1-4}$alkyl, $C_{1-3}$alkyl, $C_{1-2}$alkyl, $C_{2-6}$alkyl, $C_{3-6}$alkyl, $C_{4-6}$alkyl, $C_{5-6}$alkyl, $C_{2-5}$alkyl, $C_{3-5}$alkyl, $C_{4-5}$alkyl, $C_{2-4}$alkyl, $C_{2-3}$alkyl or $C_{3-4}$alkyl. In some embodiments, $R^1$ is methyl, ethyl, propyl, isopropyl, butyl, isobutyl, sec-butyl, tert-butyl, pentyl, isopentyl or hexyl. In certain embodiments, $R^1$ is isopropyl.

In some embodiments, $R^1$ is $C_{1-6}$alkyl-OR. In other embodiments, $R^1$ is $C_{1-5}$alkyl-OR, $C_{1-4}$alkyl-OR, $C_{1-3}$alkyl-OR, $C_{1-2}$alkyl-OR, $C_{2-6}$alkyl-OR, $C_{3-6}$alkyl-OR, $C_{4-6}$alkyl-OR, $C_{5-6}$alkyl-OR, $C_{2-5}$alkyl-OR, $C_{3-5}$alkyl-OR, $C_{4-5}$alkyl-OR, $C_{2-4}$alkyl-OR, $C_{2-3}$alkyl-OR or $C_{3-4}$alkyl-OR.

In some embodiments, $R^1$ is $C_{1-6}$alkyl-$NR_2$. In other embodiments, $R^1$ is $C_{1-5}$alkyl-$NR_2$, $C_{1-4}$alkyl-$NR_2$, $C_{1-3}$alkyl-$NR_2$, $C_{1-2}$alkyl-$NR_2$, $C_{2-6}$alkyl-$NR_2$, $C_{3-6}$alkyl-$NR_2$, $C_{4-6}$alkyl-$NR_2$, $C_{5-6}$alkyl-$NR_2$, $C_{2-5}$alkyl-$NR_2$, $C_{3-5}$alkyl-$NR_2$, $C_{4-5}$alkyl-$NR_2$, $C_{2-4}$alkyl-$NR_2$, $C_{2-3}$alkyl-$NR_2$ or $C_{3-4}$alkyl-$NR_2$.

In some embodiments, $R^1$ is $C_{1-6}$alkyl, $C_{1-6}$alkyl-OR or $C_{1-6}$alkyl-$NR_2$. In other embodiments, $R^1$ is $C_{1-3}$alkyl, $C_{1-3}$alkyl-OR or $C_{1-3}$alkyl-$NR_2$.

In some embodiments, each R is independently hydrogen or $C_{1-6}$alkyl. In other embodiments, each R is independently hydrogen or $C_{1-5}$alkyl, $C_{1-4}$alkyl, $C_{1-3}$alkyl, $C_{1-2}$alkyl, $C_{2-6}$alkyl, $C_{3-6}$alkyl, $C_{4-6}$alkyl, $C_{5-6}$alkyl, $C_{2-5}$alkyl, $C_{3-5}$alkyl, $C_{4-5}$alkyl $C_{2-4}$alkyl $C_{2-3}$alkyl or $C_{3-4}$alkyl. In certain embodiments, R each R is independently hydrogen or methyl, ethyl, propyl, isopropyl, butyl, isobutyl, sec-butyl, tert-butyl, pentyl, isopentyl or hexyl. In certain embodiments, $R^1$ is isopropyl.

In some embodiments, $R^2$ is $C_{2-6}$alkenyl. In other embodiments, $R^2$ is $C_{2-6}$alkenyl, $C_{3-6}$alkenyl, $C_{4-6}$alkenyl, $C_{5-6}$alkenyl, $C_{2-5}$alkenyl, $C_{3-5}$alkenyl, $C_{4-5}$alkenyl, $C_{2-4}$alkenyl, $C_{2-3}$alkenyl or $C_{3-4}$alkenyl. In some embodiments, $R^2$ is vinyl, allyl, propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. In certain embodiments, $R^2$ is allyl.

In some embodiments, the polymer has the structure of Formula (I), wherein $R^1$ is $C_{1-3}$alkyl; and $R^2$ is $C_{2-3}$alkenyl.

In some embodiments, the polymer has the structure of Formula (II):

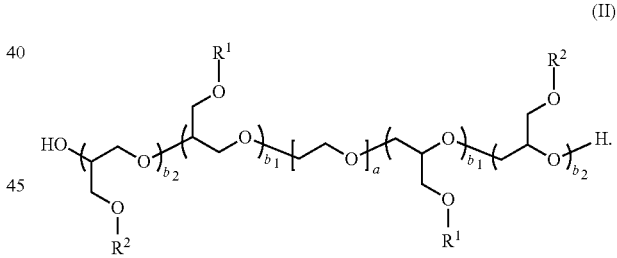

(II)

In other embodiments, the polymer has the structure of Formula (IIa):

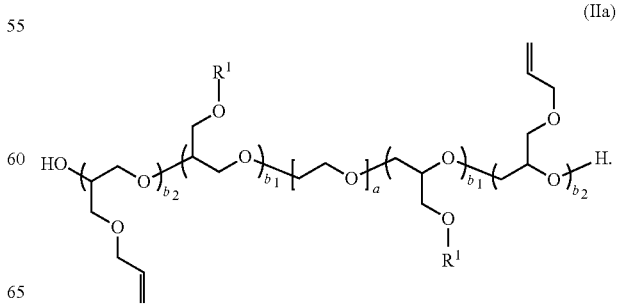

(IIa)

In some embodiments, the polymer has the structure of Formula (IIb):

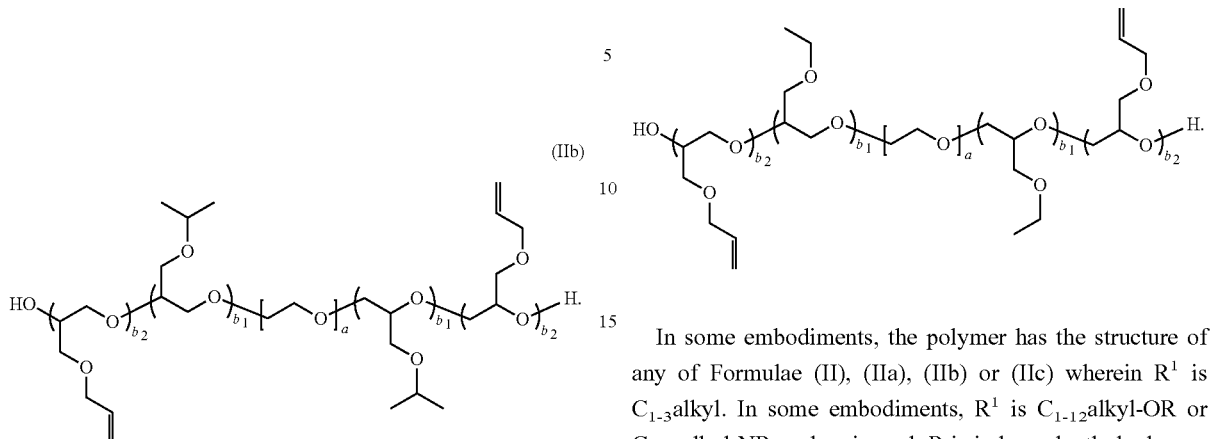

(IIb)

In some embodiments, the polymer has the structure of Formula (IIc):

(IIc)

In some embodiments, the polymer has the structure of any of Formulae (II), (IIa), (IIb) or (IIc) wherein $R^1$ is $C_{1-3}$alkyl. In some embodiments, $R^1$ is $C_{1-12}$alkyl-OR or $C_{1-12}$alkyl-NR$_2$, wherein each R is independently hydrogen or $C_{1-12}$alkyl. In other embodiments, the polymer has the structure of Formula (II), (IIa), (IIb) or (IIc) wherein $R^1$ is isopropyl.

In some embodiments, the polymer has the structure of Formula (III):

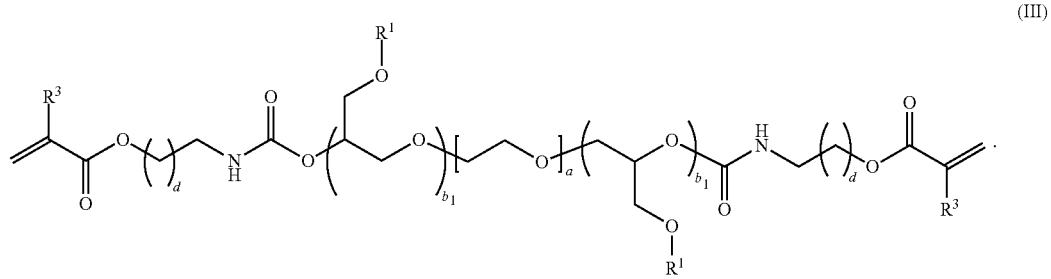

(III)

In some embodiments, the polymer has the structure of Formula (III), wherein $R^3$ is hydrogen. In other embodiments, the polymer has the structure of Formula (III), wherein $R^3$ is methyl.

In some embodiments, the polymer has the structure of Formula (IIIa):

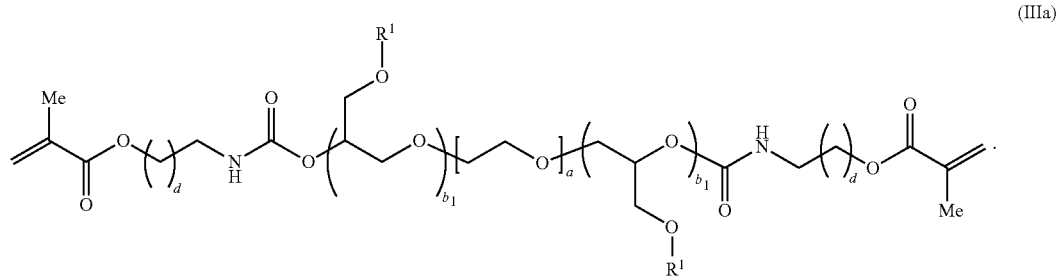

(IIIa)

The polymer of claim 1, having the structure of Formula (IIIb):

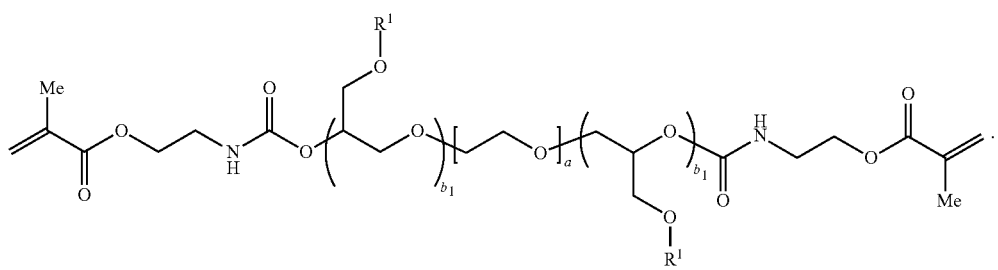

(IIIb)

In some embodiments, the polymer has the structure of any of Formulae (III), (IIIa) or (IIIb) wherein $R^1$ is $C_{1-3}$alkyl. In some embodiments, $R^1$ is $C_{1-12}$alkyl-OR or $C_{1-12}$alkyl-$NR_2$, wherein each R is independently hydrogen or $C_{1-12}$alkyl. In other embodiments, the polymer has the structure of Formula (III), (IIIa) or (IIIb) wherein $R^1$ is isopropyl.

In some embodiments, the polymer has the structure of Formula (IIIc):

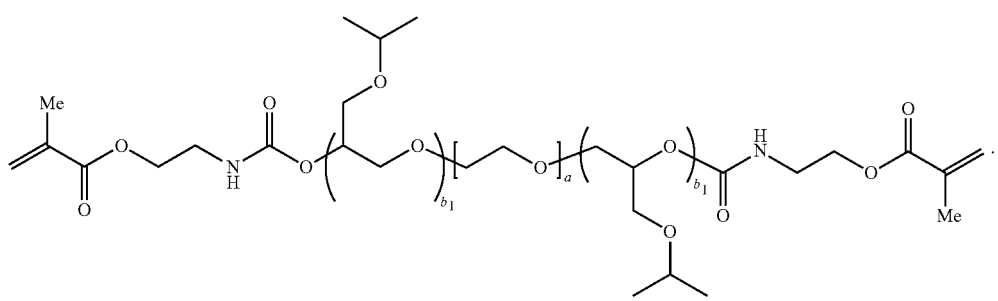

(IIIc)

In another aspect, the disclosure provides a hydrogel composition. The composition may be a triple stimuli-responsive hydrogel, which is responsive to temperature, sheer stress and light. A significant challenge for thermo-responsive and stress responsive hydrogels (e.g., F127 and iPGE based hydrogels) is that the after printing, the printed structures continue to respond to stimuli. This results in unstable printed materials, which can degrade when exposed to cold temperature or if a force is applied.

The temperature response of the hydrogel composition is important for creating homogeneous gels. At about 25° C., the hydrogel may be firm and capable of holding its form. At about 10° C., the same hydrogel may become a viscous fluid, which enables delicate materials like living cells to be incorporated in to the mixture with gentle stirring. When the mixture is warmed to ambient temperature, it becomes a gel again. This gentle method of forming a homogeneous hydrogel mixture is advantageous compared to other approaches for hydrogel formation, which include, for example, elevated temperatures, sonication, or vortexing, all of which can potentially be detrimental to delicate cells.

The response of the hydrogel composition to applied shear stress is important for extrusion printing of the composition. A shear-thinning hydrogel is ideal for this type of patterning, and can enable the formation of three-dimensional lattice structures comprised of the cell-laden hydrogel.

The response of the hydrogel composition to light is important to initiate crosslinking of the hydrogel composition to form a crosslinked hydrogel structure. The polymer hydrogel may be designed so that when it is exposed to light at particular wavelength (e.g., 365 nm), the polymer undergoes a chemical reaction that covalently crosslinks the polymer chains together. This crosslinked material is "fixed," and cannot re-dissolve when placed in water, nor exhibit temperature-responsive behavior.

In some embodiments the hydrogel composition may include a polymer of Formula (I) and an aqueous media. The polymer may be present in an amount between about 10 weight percent and about 50 weight percent of the hydrogel composition. In other embodiments, the polymer may be present in the hydrogel composition in an amount between about 10 weight percent and about 45 weight percent, about 10 weight percent and about 40 weight percent, about 10 weight percent and about 35 weight percent, about 10 weight percent and about 30 weight percent, about 10 weight percent and about 25 weight percent, about 10 weight percent and about 20 weight percent, about 10 weight percent and about 15 weight percent, about 15 weight percent and about 45 weight percent, about 15 weight percent and about 40 weight percent, about 15 weight percent and about 35 weight percent, about 15 weight percent and about 30 weight percent, about 15 weight percent and about 25 weight percent, about 10 weight percent and about 20 weight percent, about 15 weight percent and about 20 weight percent, about 15 weight percent and about 25 weight percent or about 15 weight percent and about 20 weight percent. In other embodiments, the polymer may be present in the hydrogel composition in an amount between about 12 weight percent and about 22 weight percent, about 12 weight percent and about 18 weight percent, about 14 weight percent and about 22 weight percent or about 14 weight percent and about 18 weight percent of the hydrogel composition.

The aqueous media of the polymer composition may be any liquid capable of solubilizing the polymer of Formula (I). In some embodiments, the aqueous media is water, an aqueous buffer or saline. The aqueous may be selected to be compatible with the loading agent of the hydrogel composition and with the chemical process that the crosslinked hydrogel structure will be used to catalyze. For example, when the loading agent is a marine organism or the chemical process is to occur in saltwater, the aqueous media may be saline. Other examples of aqueous media includes synthetic complete (SC), yeast extract peptone dextrose (YPD), lysogeny broth (LB), RAC1, COREs, Guillard's F/2, and rich media (RM).

In some embodiments, the hydrogel composition may form a shear-thinning gel between about 18 and about 45° C. In other embodiments, the hydrogel composition forms a shear-thinning gel between about 20 and about 30° C., between about 18 and about 25° C. between about 20 and about 25° C., between about 18 and about 22° C., between about 22 and about 30° C. or between about 22 and about 28° C.

In some embodiments the hydrogel composition may further include a photoinitiator. The photoinitiator can be any molecule known in the art to produce a radical species when exposed to a certain wavelength of light. For example, the initiator may be a peroxide, azobisisobutyronitrile or 2-hydroxy-2-methylpropiophenone. Other photoinitiators include benzophenone, ethyl 2,4,6-trimethylbenzoylphenyl phosphinate, 1-hydroxy-cyclohexyl-phenyl-ketone, 2-hydroxy-2-methyl-1-phenyl-1-propanone, 2,2-dimethoxy-2-phenyl acetophenone, 2-hydroxy-1-[4-(2-hydroxyethoxy)phenyl]-2-methyl-1-propanone, and diphenyl (2,4,6-trimethylbenzoyl)-phosphine oxide.

The photoinitiator is present in an amount between about 0 weight percent and about 20 weight percent of the polymer. In some embodiments, the photoinitiator is present in an amount between about 1 weight percent and about 20 weight percent, 1 weight percent and about 15 weight percent, 1 weight percent and about 10 weight percent, 1 weight percent and about 5 weight percent, 3 weight percent and about 20 weight percent, 3 weight percent and about 15 weight percent, 3 weight percent and about 10 weight percent, 3 weight percent and about 5 weight percent, 5 weight percent and about 20 weight percent, 5 weight percent and about 15 weight percent, or 5 weight percent and about 10 weight percent of the polymer In some embodiments the hydrogel composition may further include a loading agent. The loading agent can be any material, soluble or insoluble that can be mixed with the hydrogel composition prior to extrusion printing. For example, the loading agent can be a pharmaceutical drug, a hydrophobic additive, an organic or inorganic chemical substance, a catalyst, nanomaterials such as nanoparticles, nanotubes, and graphene, a polymer, a biopolymer, or a living cell.

In certain embodiments the loading agent is a living cell. The cell may be a plant or animal cell, protist, fungal, or bacterial cells. The cell may be a freshwater or marine organism. In some embodiments the living cell is an algal cell. In another embodiment, the living cell is a yeast cell. The cell may also be a modified or transformed cell. For example, the living cell can be a yeast cell transformed with a plasmid that produces an neuropeptide, and the neuropeptide may be of pharmacological use.

The living cell may be able to participate in a chemical process. In some embodiments the living cell is capable of catalyzing or promoting a chemical reaction. In other embodiments, the living cell may be able to participate in a fermentation process. For example, the living cell may be an algal cell capable of photoautotrophic growth, such as *Chlamydomonas*. In another example, the algae may be able to capture heavy metals and trace organics, which would be useful for water purification of water and waste water treatment.

In another aspect, the disclosure provides a crosslinked hydrogel structure including a polymer of Formula (I), an aqueous media, and a loading agent, wherein the polymer includes crosslinks derived from the alkene groups of $R^2$ in different polymer chains, or the polymer includes crosslinks derived from the alkene groups of the (meth)acrylate derivative in different polymer chains. Also disclosed is a method for forming a crosslinked hydrogel structure. The method may involve subjecting a polymer composition including a polymer of Formula (I), an aqueous media, a photoinitiator and a loading agent to UV light to initiate crosslinking between and the alkene groups of $R^2$ in different polymer chains, or between the alkene groups of the (meth)acrylate derivative in different polymer chains.

When the polymer of the hydrogel composition have the structure of any of Formula (II), (IIa), (IIb) or (IIc), the crosslinks of the crosslinked hydrogel structure are derived from the alkene groups of $R^2$ in different polymer chains. That is, the crosslinked hydrogel structure is formed by subjecting a hydrogel composition including a polymer of Formula (II), (IIa), (IIb) or (IIc) to crosslinking conditions, optionally in the presence of a photoinitiator, to crosslink the alkene groups of $R^2$ in different polymer chains.

Similarly, when the polymer of the hydrogel composition have the structure of any of Formula (III) or (IIIa)-(IIIc), the crosslinks of the crosslinked hydrogel structure are derived from the alkene groups of (meth)acrylate derivative in different polymer chains. That is, the crosslinked hydrogel structure is formed by subjecting a hydrogel composition including a polymer of Formula (III) or (IIIa)-(IIIc) to crosslinking conditions, optionally in the presence of a photoinitiator, to crosslink the alkene groups of (meth)acrylate derivative in different polymer chains.

In some embodiments, the crosslinking is performed on the extruded hydrogel composition. In other embodiments, the crosslinking is performed on the hydrogel composition directly (i.e., without extrusion printing).

Crosslinking of the hydrogel composition to provide a crosslinked hydrogel structure significantly changes the properties of the hydrogel composition. Following crosslinking, the crosslinked hydrogel structure has improved mechanical robustness and viscoelastic properties, is not soluble in aqueous solution and maintains transparency.

For hydrogel composition including the polymer of Formula (III) crosslinking occurs between the methacrylate groups, and the urethane moieties offer hydrogen bonding motifs that can help preserve elasticity and mechanical robustness of printed structures after crosslinking.

In another aspect, the disclosure provides a method for extrusion printing a polymer composition. The method may involve:
  obtaining a hydrogel composition including a polymer of Formula (I), and an aqueous media; and
  extrusion printing the composition to provide an extruded hydrogel composition.

In some embodiments, the hydrogel composition further includes a photoinitiator. In other embodiments, the hydrogel composition further includes a loading agent. In some embodiments, the hydrogel composition further includes a photoinitiator and a loading agent.

In some embodiments, the hydrogel composition is printed into a multi-layer patterned structure. The hydrogel composition can be transferred into the printer syringe by cooling the hydrogel composition to provide a liquid and pouring the solution. Upon warming to ambient temperature, the hydrogel composition can become a gel that can be printed via extrusion to provide an extruded hydrogel composition. The thickness of the extruded hydrogel composition can be controlled by modifying the nozzle diameter, as well as the print speed. For example, the nozzle can be a 210, 260, or 410 μm diameter. As the speed at which the nozzle moves across the printing surface is increased, the diameter of the printed strand is decreased. The extruded hydrogel composition can be printed in a grid of up to 40 layers demonstrating without the lines supporting the structure buckling or sagging.

The temperature at which the extrusion printing is performed will depend on the properties of the hydrogel composition being printed. In some examples, the extruded hydrogel composition is a gel at ambient temperature, so the extrusion printing may be performed at ambient temperature. Thus, the temperature can range from 10° C. to 45° C. In other embodiments, the hydrogel composition is cooled below ambient temperature to provide the hydrogel composition as a liquid for homogenously incorporating the loading agent.

The method may also further involve subjecting the extruded hydrogel composition to crosslinking conditions to provide a crosslinked hydrogel structure. For example, UV light may be used to initiate crosslinking between the alkene groups of $R^2$ in different polymer chains, or between the alkene groups of the (meth)acrylate derivative in different polymer chains to form a crosslinked hydrogel structure.

Crosslinking of the extruded hydrogel composition will introduce a permanently crosslinked network of polymer chains and hence will produce a mechanically robust hydrogel structure. This will broaden the scope of the hydrogel structures for various applications in aqueous media such as in chemical catalysis, production of antibiotics, bio fuels cells, waste water treatment, etc. The crosslinked hydrogel structure enables the use of 3D printed objects in such applications where traditional 3D printed hydrogels are prone to degradation.

The extruded hydrogel composition can be cured for about 1 second to about 10 minutes by exposure to irradiation. The irradiation wavelength is in the range of 100 nm to 700 nm. In some embodiments, the irradiation wavelength is in the range of 200 nm to 700 nm, 100 nm to 650 nm, 200 nm to 700 nm, 200 nm to 650 nm, 300 nm to 700 nm, 350 nm to 700 nm, 400 nm to 700 nm, 450 nm to 700 nm or 500 nm to 700 nm. In other embodiments, the irradiation wavelength is in the range of 200 nm to 600 nm, 100 nm to 550 nm, 200 nm to 600 nm, 200 nm to 550 nm, 300 nm to 600 nm, 350 nm to 600 nm, 400 nm to 600 nm, 450 nm to 600 nm or 500 nm to 600 nm.

In some embodiments, the curing is performed in a UV cure box having 365 nm wavelength irradiation with a power of 3.4 mW/cm$^2$. Crosslinking allows for robust hydrogel structures to be held with forceps without damaging the structure.

In another aspect, the disclosure provides a method for performing a chemical reaction involving the loading agents. The method may involve:
  subjecting a crosslinked hydrogel structure to a reactant capable of undergoing chemical reaction; and
  recovering the product of the chemical reaction.

The photoautotrophic growth ability of green algae using carbon dioxide as the sole source of carbon and light as the source of energy may be useful in the development of new algal based carbon capture systems. These algal-based carbon capture systems can be significantly important in applications such as biomass and biofuel productions, production of food additives, and pharmaceuticals. For example, yeast cells can be used to produce ethanol from basic feedstocks.

In another embodiment, yeast cells are used to transform glucose and other glycoside feedstocks into ethanol.

In another embodiment, cells may be able to capture heavy metals and trace organics. Such applications are promising in environmental challenges like water purification and waste water treatment.

Experimental Methods:

Materials and Methods

Characterization. 1H NMR spectroscopy was carried out on a Bruker AVance 300 MHz or 500 MHz spectrometer in deuterated chloroform (CDCl3). Chemical shifts are reported in delta (δ) units, expressed in parts per million (ppm) downfield from tetramethylsilane using the residual protonated solvent as an internal standard (for CDCl3 1H: 7.26 ppm). Gel permeation chromatography (GPC) was performed at room temperature on a Waters instrument with two Viscotek columns (I-MBMMW-3078, I-series mixed bed and I-MBLMW-3078, I-series mixed bed) arranged in series, and a Waters 2414 differential refractometer. Chloroform stabilized with 0.1% v/v triethylamine was used as the mobile phase.

Rheology. Dynamic oscillatory experiments were performed on a TA Instruments DHR (Dynamic Hybrid Rheometer) equipped with a peltier using a 20 mm parallel plate geometry. Samples were equilibrated in an ice bath for at least 30 min and then were carefully loaded onto the Peltier plate at 5° C. and a pre-shear experiment was applied to eliminate the bubbles from the sample cell, and a solvent trap was utilized to minimize solvent evaporation. The sample was equilibrated at 25° C. for 8 min before each run. Hydrogel yield stresses were measured under oscillatory stress (frequency 1 Hz, 25° C.) starting with an initial stress of 1 Pa up to 104 Pa. Viscosity versus shear rate experiments were performed in the range between 0.01 and 10 of shear rate. Cyclic shear thinning tests (frequency 1 Hz) were performed at 25° C. using alternating strains of 1% for 5 min and 100% for 3 min per cycle, to investigate the shear-thinning and recovery behavior of the hydrogels. Temperature ramp experiments were performed at 1 Hz from 5-50° C. at 2° C./min. UV curing was performed using a fully integrated smart swap LED UV curing accessory. A 60 s long irradiation of 365 nm light at 5 mW/cm2 intensity was triggered 120 s into the experiment, and the sample was monitored for a total of 270 s at 1% of strain and at 1 Hz.

Materials. All chemicals were used as received from Sigma-Aldrich unless otherwise specified. THF and CH2Cl2 were collected from a Glass Contour solvent purification system and used immediately thereafter. Potassium naphthalenide was prepared from potassium metal and naphthalene in dry THF and allowed to stir with a glass-coated stir-bar for 24 h at room temperature before use. Glycidyl isopropyl ether was distilled, sequentially, from calcium hydride and butyl magnesium chloride, and degassed via several freeze-pump-thaw cycles before use.

Polymer Preparation
Synthesis of IPGEx Triblock.

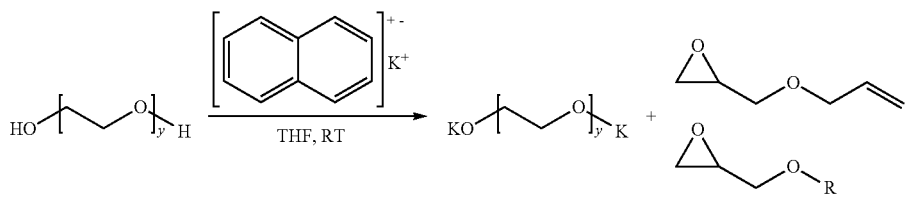

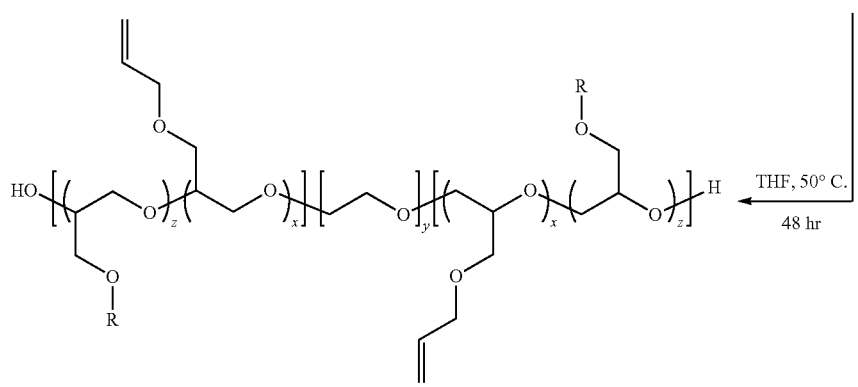

All polymerizations were carried out on a Schlenk line in custom thick-walled 5-neck glass reactors fitted with threaded ACE threads under an argon atmosphere. The reactors were fitted with burettes containing pre-measured quantities of THF and glycidyl isopropyl ether, respectively, and a glass arm containing a port for a 15 mm rubber septum and a connector to the Schlenk line. The reactors were dried under vacuum then refilled with argon five times. Poly (ethylene glycol) (MW=8000 Da; 10.88 g, 1.36 mmol) was added, dried under vacuum overnight, and dissolved in dry THF (100 mL) at 50° C. Under an argon atmosphere and using a gas-tight syringe, a THF solution of potassium naphthalenide was added through a 15 mm rubber septum until a green color persisted in solution, indicating the deprotonation of all terminal alcohol groups. Glycidyl isopropyl ether (4.50 g, 38.7 mmol) was then dispensed from the burette to initiate the polymerization. The reaction was stirred for 48 h and terminated with degassed methanol (5 mL). The volume of the reaction mixture was reduced by roughly half, and the mixture was precipitated into ethyl ether. Centrifugation of the suspension and drying under reduced pressure afforded the desired polymer, IPGEx, as a white solid (13.46 g, 88% yield). 1H NMR (300 MHz, CDCl3): δ 3.62 (s, 880H), 1.12-1.10 (d, 153H). GPC: $M_n$=10446 Da; Mw/Mn=1.1.

Statistical copolymers PiPGE-stat-PAGE-b-PEG-b-PiPGE-stat-PAGE were synthesized by changing the iPGE and AGE monomer feed ratios, as well as the molar ratios of the monomers to PEG macroinitiator. The polymer composition was determined using the integration values of the ethylene glycol backbone (3.4-3.6 ppm) and allyl, vinyl, and methyl protons at 4, 5.2, 5.9, and 1.15 ppm, respectively, from the allyl glycidyl ether unit and isopropyl glycidyl ether unit in the $^1$H NMR spectrum. The resulting $M_n$ for polymers 3, 4, and 5 were 1.2k-b-8k-b-1.2k g/mol (DP 2.4 PAGE and DP 19.2 PiPGE), 1.4k-b-8k-b-1.4k g/mol (DP 4.4 PAGE and DP 19.2 PiPGE), and 1.7k-b-8k-b-1.7k g/mol (DP 16 PAGE and DP 13.2 PiPGE), respectively (Table 3).

Ethyl and allyl glycidyl ether were also co-polymerized to afford PEGE-stat-PAGE-b-PEG-b-PEGE-stat-PAGE (polymer 6). Analysis by $^1$H NMR spectroscopy showed that polymer 6 was polymerized in the same manner as above and the composition was determined by using the integration values of the ethylene glycol backbone (3.4-3.6 ppm) and the allyl, vinyl, and methyl protons at 4, 5.2, 5.9, and 1.2 ppm respectively from the allyl glycidyl ether unit and ethyl glycidyl ether unit in the $^1$H NMR spectrum. The resulting $M_n$ for polymer 6 was 1.7k-b-8k-b-1.7k g/mol (DP 11.2 PEGE and DP 19.2 PAGE) (Table 3).

TABLE 3

Representative polymer compositions with different monomer ratios

| Composition | Alkyl Ethers | P(R)GE/PAGE-b-PEG-b-P(R)GE/PAGE | DP AGE | DP iPGE | DP EGE | $D^b$ |
|---|---|---|---|---|---|---|
| Polymer 3 | AGE/iPGE | 1.2k-b-8k-b-1.2k | 2.4 | 17.8 | — | 1.10 |
| Polymer 4 | AGE/iPGE | 1.4k-b-8k-b-1.4k | 4.4 | 19.2 | — | 1.11 |
| Polymer 5 | AGE/iPGE | 1.7k-b-8k-b-1.7k | 16 | 13.2 | — | 1.12 |
| Polymer 6 | AGE/EGE | 1.7k-b-8k-b-1.7k | 19.2 | — | 11.2 | 1.11 |

Synthesis of IPGEx-UDM Triblock.

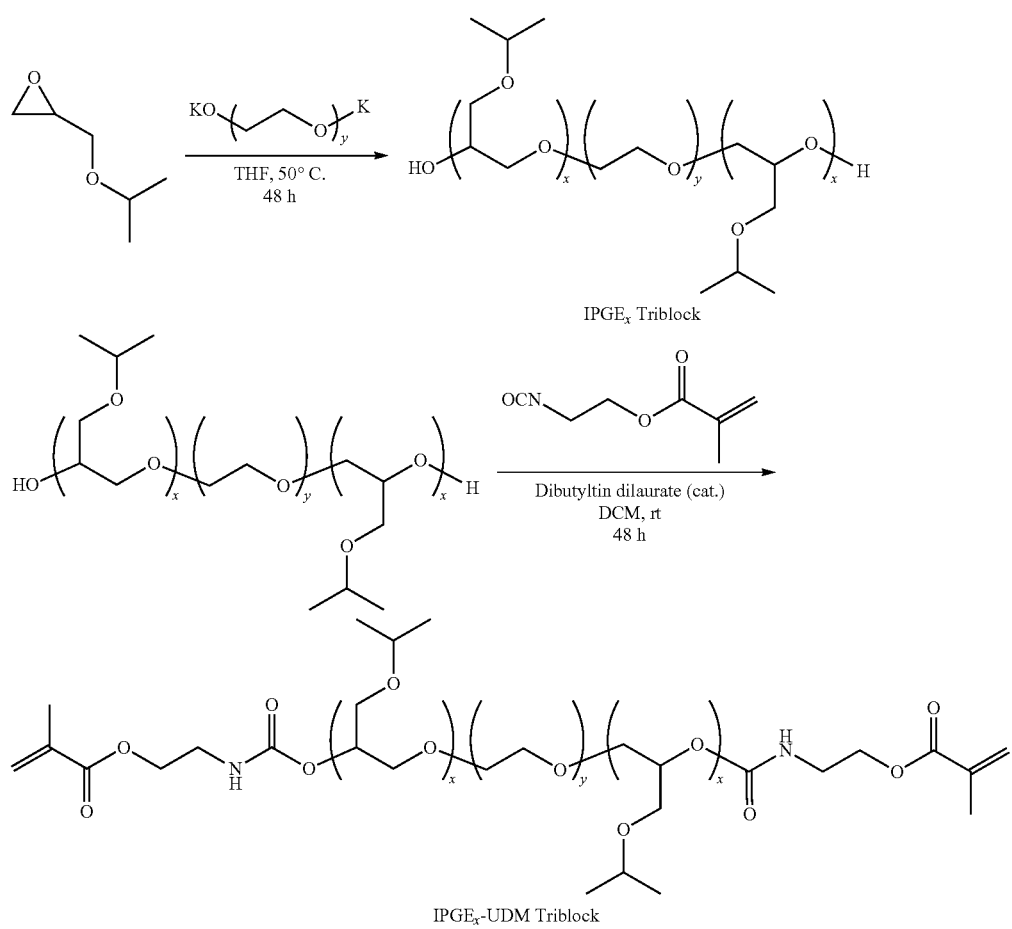

In a 250 mL round bottom flask, IPGEx Triblock copolymer (11.84 g, 1.09 mmol) was dissolved in CH2Cl2 (100 mL). Under a nitrogen atmosphere, 2-isocyanatoethyl methacrylate (1.50 mL, 10.9 mmol) and dibutyltin dilaurate (0.13 mL, 0.22 mmol) were sequentially added via syringe. The resulting mixture was stirred for 48 h at room temperature, transferred directly into a dialysis membrane, and dialyzed against methanol for 24 h, exchanging the dialysate with fresh solvent a minimum of three times. Concentrating the contents of the dialysis bag under reduced pressure afforded the desired polymer as a white solid (7.05 g, 53% yield). The degree of endgroup functionalization (fn) was determined by 1H NMR spectroscopy, by comparing the integration of the signal attributable to the methyl groups of IPGE ($\delta$ 1.12 ppm) with that of the terminal methine protons ($\delta$ 4.91 ppm) located adjacent to the newly formed urethane groups. 1H NMR (300 MHz, CDCl3): $\delta$ 6.10 (s, 1.31H), 5.57 (s, 1.37H), 5.21 (br, 1H), 4.91 (m, 1.37H), 4.20 (t, 3.07H), 3.63 (m, 897H), 1.93 (s, 4.63H), 1.13-1.13 (d, 153H). fn=0.70.

Hydrogel Preparation
IPGEx Hydrogels.

The PiPGE-b-PEG-b-PiPGE triblock structure demonstrated improved mechanical properties compared to F127 and formed hydrogels at lower concentrations. Furthermore, the lower gelation temperatures of 13 and 15 wt % hydrogels reduced the potential variability in the gel mechanical properties which enabled more consistent printing at room temperatures. In contrast, a 15 wt % F127 hydrogel, which exhibited a gel point at 34° C. may encounter more variabilities with small room temperature fluctuations. The physical network of the disclosed hydrogels might reach the percolation threshold at lower concentrations and temperatures compared to F127. This result may be attributed to both the physical entanglements and reinforcing bridged loops between micelles.

These hydrogels were further characterized by rheometry. FIG. 1 compares the dynamic elastic (G') and viscous (G") moduli for 18 wt % concentration of polymer 4, as well as a 20 wt % concentration of polymer 6. The results confirm that both hydrogels exhibit a reversible sol-gel transition. The gelation temperature (which is defined by the intersection of the G' and G" curves) is below room temperature for polymers 4 and 6 (13.5 and 14.3° C., respectively). Thus, at ambient temperature, the material occupies a gel state, but when the sample is brought to a temperature below its gelation temperature, the material occupies its sol state. This reversible temperature response is an important feature of these hydrogel compositions as the composition can be transferred into a 3D printer in its liquid state by cooling below its $T_{gel}$, but then printed at room temperature in its gel state.

Figure 3:
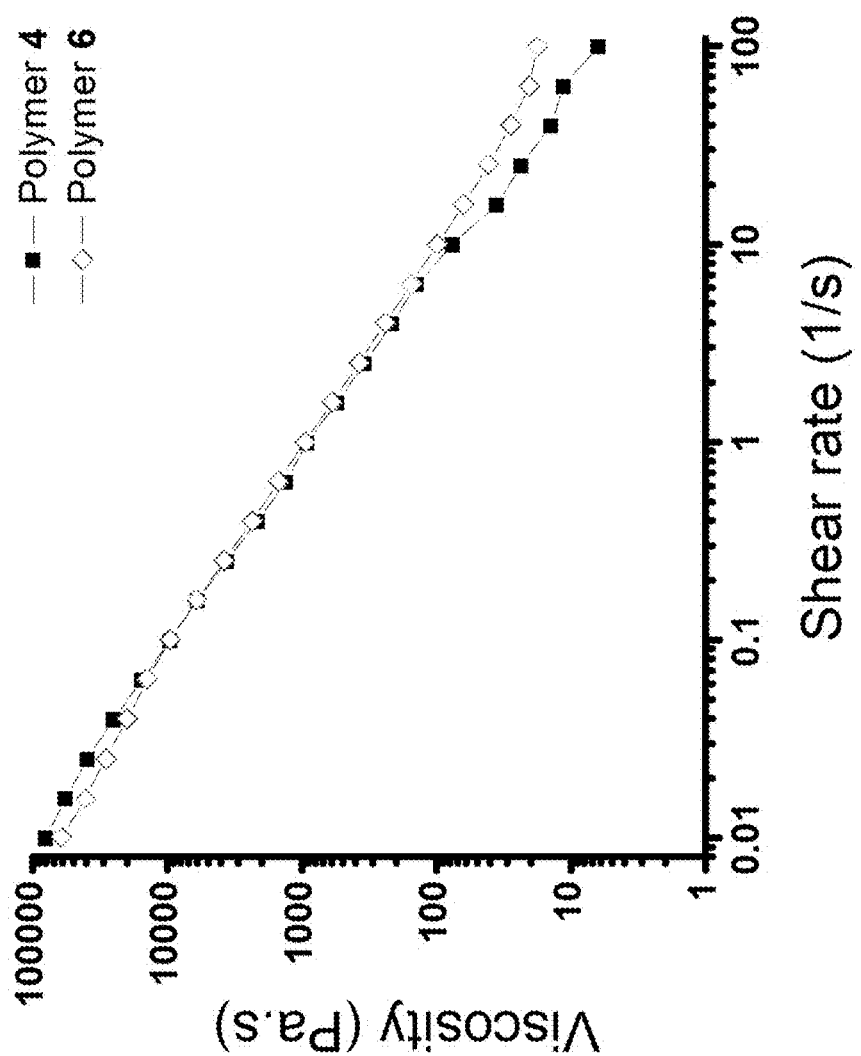
FIG. 3 is a viscosity versus shear rate profile showing non-Newtonian behavior and shear-thinning properties of 18 wt % polymer 4 (black) and 20 wt % polymer 6 (gray) hydrogels, in accordance with an example embodiment.

An ideal material for extrusion through a small diameter nozzle in direct-write 3D printing is a shear-thinning polymer composition. Therefore, the shear-thinning behavior and the gel yield stress at 25° C. was determined. FIG. 3 shows that the hydrogels including polymer 4 and polymer 6 have linearly decreasing shear viscosities as the shear rate increases. The viscosity versus shear rates are similar between 18 wt % polymer 4 and 20 wt % polymer 6. These results indicate the gels are non-Newtonian fluids and shear thinning.

Figure 5:
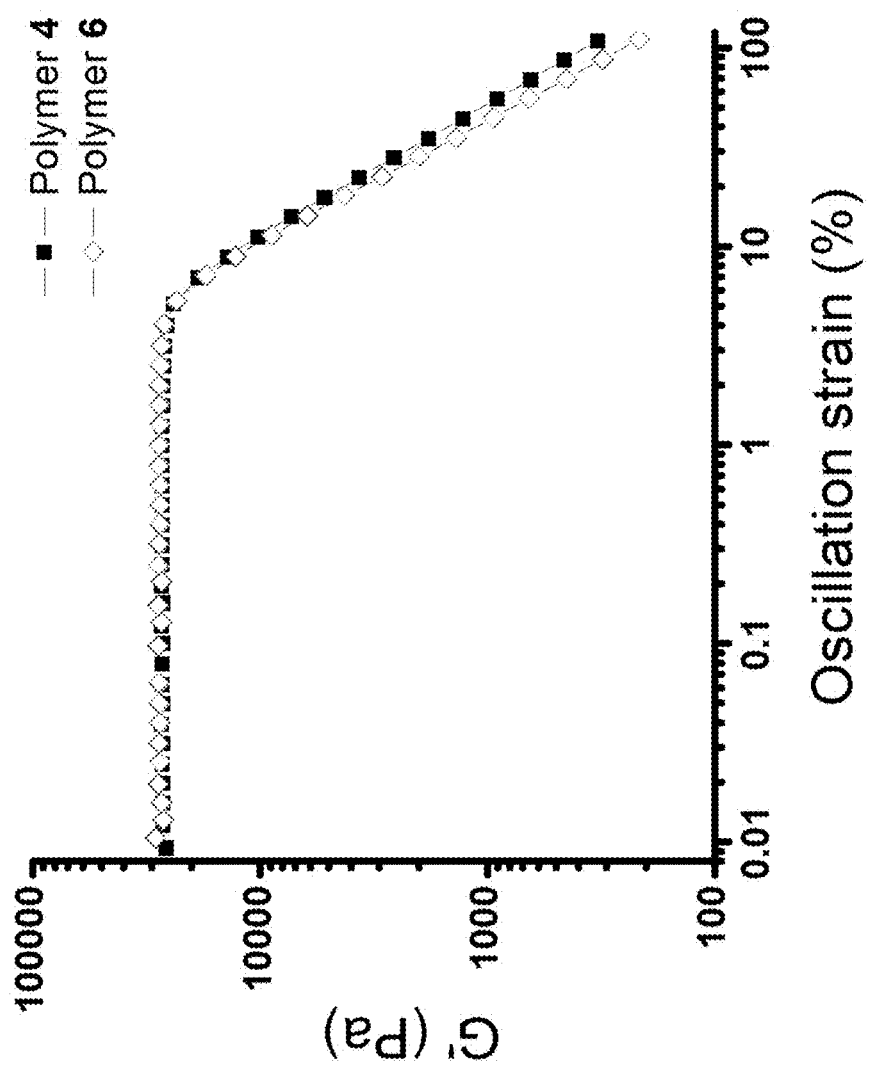
FIG. 5 is a graph depicting modulus versus strain showing the yield strain of 18 wt % polymer 4 (black) and 20 wt % polymer 6 (gray) hydrogels, in accordance with an example embodiment.

The gel yield stress, an important parameter that implies the force necessary for gel extrusion, was also determined. The gel yield stress provides an indirect indication of the gel strength as it supports subsequent stacked layers during 3D printing. In other words, an extruded hydrogel composition with a higher yield stress can support more stacked layers without printing defects, such as sagging, than a gel with a low yield stress. FIG. 5 suggests that the incorporation of ethyl glycidyl ether allows for greater allyl glycidyl ether content to obtain nearly identical yield stress results. Hydrogels including polymers 4 and 6 have 7.7 kPa at 18 wt % and 8.3 kPa at 20 wt %. These results suggest that these polymer compositions will have similar printing performance and printing quality.

Figure 7:
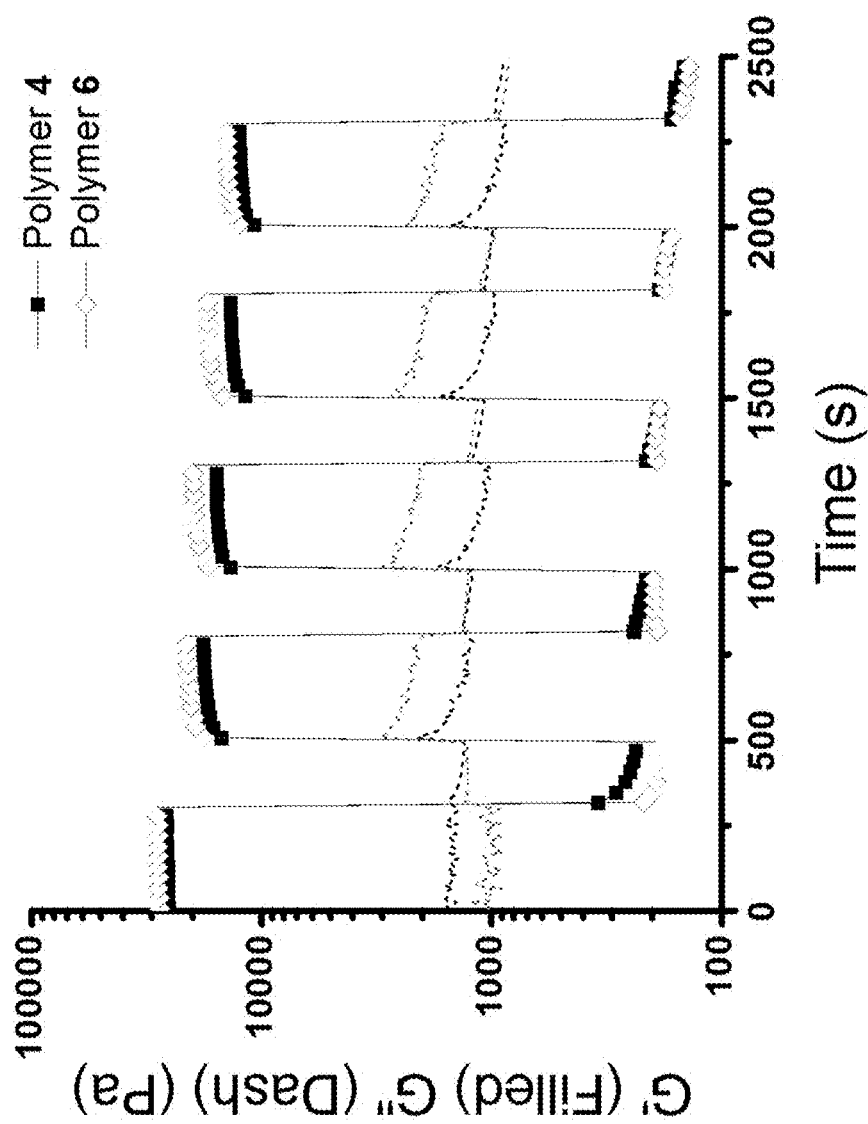
FIG. 7 is a graph of cyclic shear-thinning of 18 wt % polymer 4 (black) and 20 wt % polymer 6 (gray) hydrogels, showing G', storage modulus, response and instantaneous recovery to high (100%) and low (1%) oscillatory strains, in accordance with an example embodiment.

The reversible (and self-healing) nature of the physical cross-links that exist within these hydrogel networks manifests itself in the instantaneous response of the gel modulus to changes in the applied strain as illustrated in FIG. 7. In this experiment, 18 wt % polymer 4 and 20 wt % polymer 6 hydrogels were subjected to 5 cycles of low (1%) strain for 5 min and high (100%) strains for 3 min. All the hydrogels exhibited a marked decrease in the G' moduli at high strains and immediate recovery at low strains for each cyclic testing. Polymer 4 had G' moduli of ~17.5 kPa and 0.2 kPa at 1% and 100% strains, respectively. Polymer 6, being a slightly stronger gel with higher concentration, had G' moduli of ~20.8 kPa and 0.2 kPa at 1% and 100% strains, respectively. All the hydrogels demonstrated the G' response to high and low strains occurred in less than 15 seconds. This rapid and reversible shear-thinning behavior is attributed to the disruption of the physical network under large shear deformations while the recovery was due to the rapid reformation of the transient network, which was promoted by hydrophobic interaction. Furthermore, the hydrogel compositions displayed minimal mechanical hysteresis between strain cycles, a desirable property for direct-write 3D printing. The small degree of hysteresis between the first and second cycles was likely due to the initial equilibration at 0% strain for 8 minutes leading to the observed higher G' in the first cycle. This rapid and reversible modulus response to shear stress renders these materials suitable for direct-write 3D printing because they can be easily extruded during printing while maintaining sufficient mechanical integrity necessary to support the next printed layer.

IPGEx-UDM Hydrogels.

The preparation of a 15 wt % hydrogel is described as a representative example. IPGE12.5-UDM triblock copolymer (1.5 g) and deionized water (8.5 g) were weighed into a 20 mL glass scintillation vial. A magnetic stir bar was added and the vial was sealed, and the mixture was placed in an ice bath with constant stirring. After complete dissolution of the polymer (approx. 24 h), the vial was removed from the ice bath and equilibrated at room temperature for ten minutes to afford a clear, transparent hydrogel.

In a specific example, IPGE2.5-UDM triblock copolymer was dissolved in deionized water to prepare 13 and 15% (w/w) solutions. First, the required quantities of the IPGE12.5-UDM and deionized water were weighed in a sealed glass vial. Then the mixtures were kept on ice with constant stirring. After complete dissolution of the IPGE12.5-UDM, the vials were incubated at room temperatures for ten minutes to obtain clear transparent hydrogels.

Figure 2:
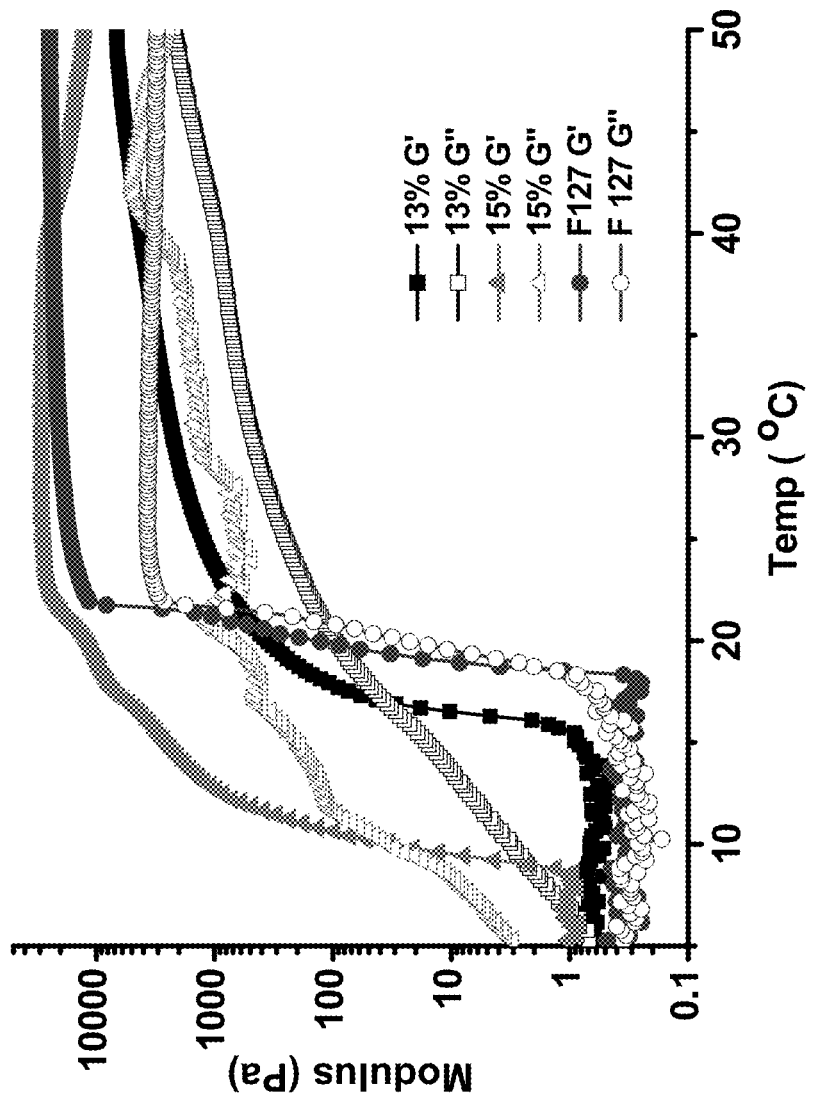
FIG. 2 is an oscillatory viscoelastic temperature ramp curve of the storage (G') and loss (G") moduli of 13 and 15 wt % IPGE12.5-UDM and 20 wt % of F127 hydrogels, in accordance with an example embodiment.

At concentrations of 15 and 13 wt %, IPGE12.5-UDM formed transparent hydrogels at room temperature. The mechanical and thermoresponsive behavior of the hydrogels at varying concentrations in water were investigated using a rheometer. FIG. 2 compares the dynamic storage (G') and loss (G") moduli for 13 and 15 wt % solutions of IPGE12.5-UDM, as well as a 20 wt % solution of F127 over a wide range of temperature (5-50° C.). All of the hydrogels displayed thermoresponsive gelation below room temperature. The hydrogels at 13 and 15 wt % exhibited gelation temperatures (Tgel; temperature at which G' crosses G") of 17.0 and 10.1 C, respectively. Both of the samples have a lower Tgel compared to 15 wt % F127 (Tgel=34° C.), suggesting that the structure and composition of IPGE12.5-UDM plays a significant role in determining the mechanical properties of the resulting hydrogels.

Furthermore, the hydrogels at 13 and 15 wt % demonstrated a higher gel modulus compared to F127 at identical hydrogel weight percentages. At 13 and 15 wt %, hydrogels have G' (T=25° C.) values of 1.3 and 27.2 kPa, respectively, whereas a 15 wt % F127 solution remains a liquid at that temperature. Thus, the mechanical properties of the hydrogel can be tuned on demand simply by changing the concentration of IPGE12.5-UDM. In order to obtain comparable room temperature G' values of F127, a 20% solution of F127 has a G' (T=25° C.) of 16.6 kPa.

An ideal material for extrusion through a small diameter nozzle in direct-write 3D printing is a shear-thinning polymer hydrogel ink. The shear-thinning behavior and gel yield stress at 25° C. for the hydrogels in FIG. 4 indicates that the three gels obtained from 20 wt % F127, 13 wt % and 15 wt % of IPGE12.5-UDM have linearly decreasing shear viscosities as the shear rate increases. The viscosity versus shear rate trend increased from 13 wt % IPGE12.5-UDM to 20 wt % F127, and 15 wt % IPGE12.5-UDM as expected based on the storage moduli of the gels at room temperature. These results indicate that the hydrogels are non-Newtonian fluids and capable of furnishing the shear-thinning behavior.

Figure 6:
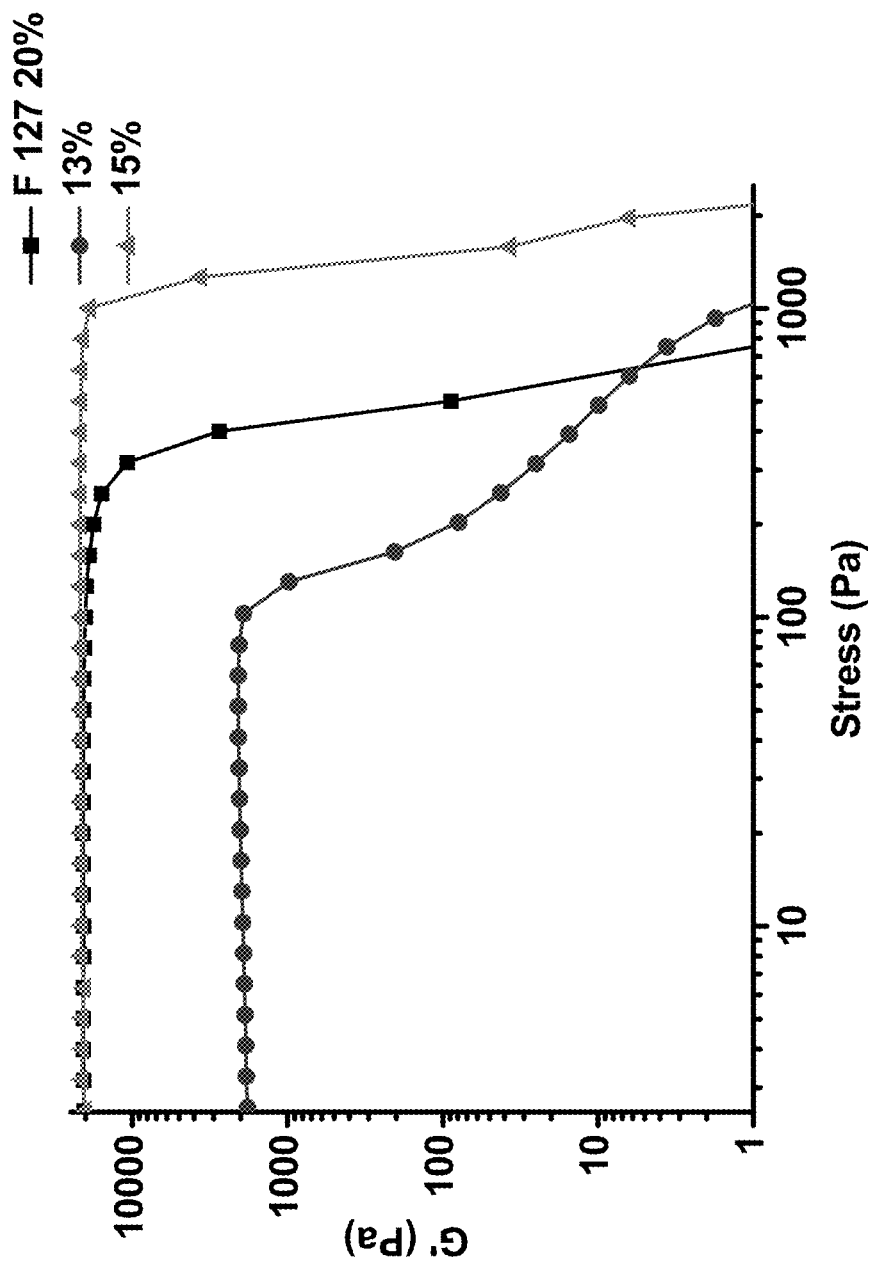
FIG. 6 is a graph depicting storage modulus versus stress showing the corresponding yield stress for 20 wt % F127, 13 wt % and 15 wt % IPGE12.5-UDM hydrogels, in accordance with an example embodiment.

Gel yield stress is an important parameter that implies the force necessary to extrude the hydrogel through a nozzle. The gel yield stress also provides an indirect indication of the hydrogel strength as it supports subsequent stacked layers during extrusion (e.g., 3D printing). In other words, a gel with a higher yield stress will be capable of supporting more stacked layers without printing defects (e.g., sagging) than a gel with a low yield stress. FIG. 6 suggests that the hydrogels of IPGE12.5-UDM at 13 wt % and 15 wt % afforded yield stress of 134 and 1226 Pa, respectively, compared to 363 Pa for the F127 gel at 20 wt %. These results strongly suggest that IPGE12.5-UDM is promising for a better printing performance and enhanced printing quality at 15 wt % than F127.

Figure 8:
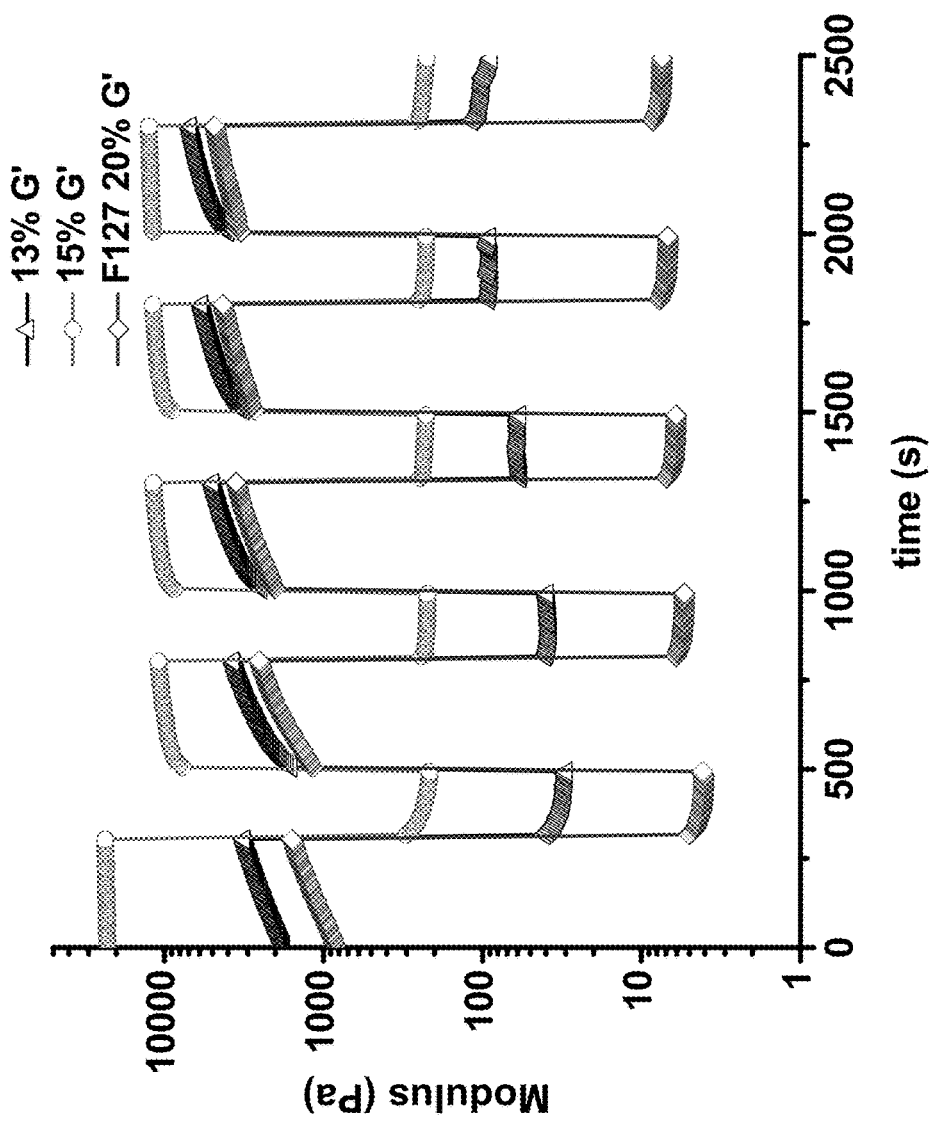
FIG. 8 is a graph depicting cyclic shear-thinning experiment of 15 wt % and 13 w t % IPGE12.5-UDM and 20 wt % F127 hydrogels showing G', storage modulus, response and instantaneous recovery to high (100%) and low (1%) oscillatory strains, in accordance with an example embodiment.

The reversible (and self-healing) nature of the physical crosslinks that exist within the hydrogel networks manifests itself in the instantaneous response of the gel modulus to changes in the applied strain. In FIG. 8, 13 and 15 wt % hydrogels derived from IPGE12.5-UDM and 20 wt % hydrogels from F127 were subjected to five successive cycles of alternating low (1%) and high (100%) strains for 5 and 3 min, respectively. All the hydrogels exhibited a sharp decrease in the storage moduli (G') at high strains and immediate recovery at low strains for each cyclic testing. F127, the weakest gel, had G' moduli of ~2.78 and 0.006 kPa at 1 and 100% strains, respectively. IPGE12.5-UDM at 13 wt % had G' moduli of ~3.88 kPa and ~0.06 kPa at 1 and 100% strains, respectively. IPGE12.5-UDM at 15 wt %, being a stronger gel, had G' moduli of ~11.77 kPa and ~0.23 kPa at 1 and 100% strains, respectively. All the hydrogels demonstrated the G' response to high and low strains occurred in less than 15 s. This rapid and reversible shear-thinning behavior is attributed to the disruption of the physical network under large shear deformations while the recovery was due to the rapid reformation of the transient network, which was promoted by hydrophobic interaction.

Furthermore, hydrogels of IPGE12.5-UDM displayed minimal mechanical hysteresis between strain cycles, which is a desirable property for direct-write 3D printing. This rapid and reversible modulus response to shear stress renders these materials suitable as inks for direct-write 3D printing because they can be easily extruded during printing while maintaining sufficient mechanical integrity necessary to support the next printed layer.

3D Printing of Hydrogels

A direct-write printer capable of translating the x, y, and z directions at 25 μm resolution was used. The hydrogel inks were cooled to 5° C. and poured into a Nordson Optimum 10 cc fluid dispensing barrel equipped with a Metcal conical (210, 260, or 410 μm inner diameter) precision tip nozzle. The syringe was pressurized using nitrogen gas (35 psi) to extrude the gel from the nozzle at ambient temperature. The printer was controlled with an Arduino using Marlin firmware. The G-code was made with Slic3r.

Preparation of Crosslinked Hydrogel Structures

IPGEx Crosslinked Hydrogels.

Figure 4:
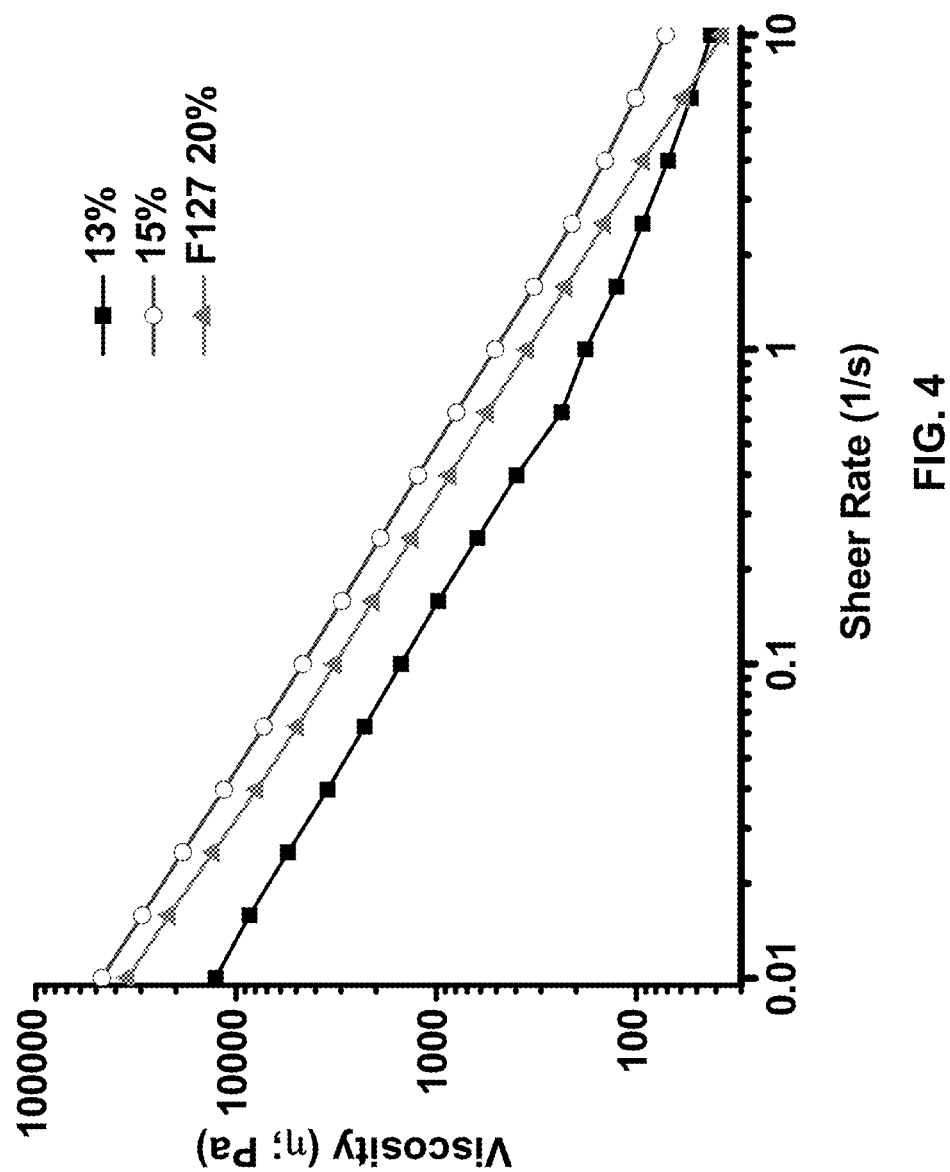
FIG. 4 is a plot of viscosity versus shear rate profile of 20 wt % F127, 13 wt % and 15 wt % IPGE12.5-UDM hydrogels at 25° C., in accordance with an example embodiment.

It was initially hypothesized that thiol-ene reactions would be necessary to cross-link the polymer chains of IPGEx hydrogels the in the presence of a photoradical generator (2-hydroxy-2-methyl propiophenone). Unexpectedly, however, the IPGEx hydrogels can undergo photo-initiated cross-linking in the absence of any dithiol cross-linking molecule. The allyl groups can undergo radical-initiated cross coupling to form covalent bonds that bridge polymer chains. Thus, for this hydrogel system, thiol-ene mediated cross-linking is not necessary to afford a covalently fixed structure. In order to investigate these cross-linking reactions further, hydrogel formulations of polymer 4 and polymer 6 were created with photoinitiator concentrations that were 0 to 5 wt % of the polymer weight (FIG. 4). Polymer 6 possesses a higher allyl glycidyl ether composition, and therefore, a higher storage modulus after UV curing as a consequence of the increased cross-link density.

Figure 9:
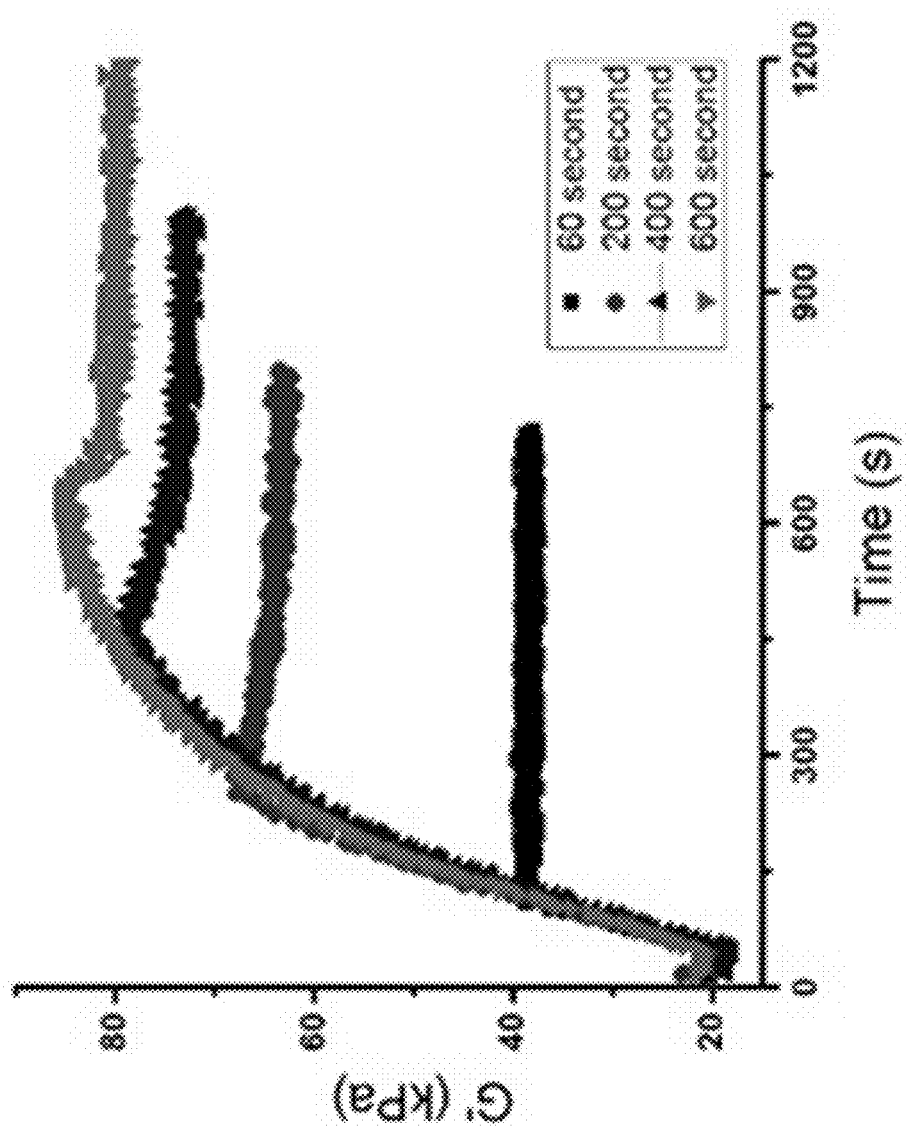
FIG. 9 is a dynamic oscillatory UV cure graph showing tunability of G' moduli by altering length of UV irradiation, in accordance with an example embodiment. The experiment was performed on polymer 5 at 20 wt % concentration and 1% photoinitiator concentration based on polymer weight with 60 second dwell time followed by 60 to 600 second cure times and a 10 minute post-cure constant strain.
Figure 10:
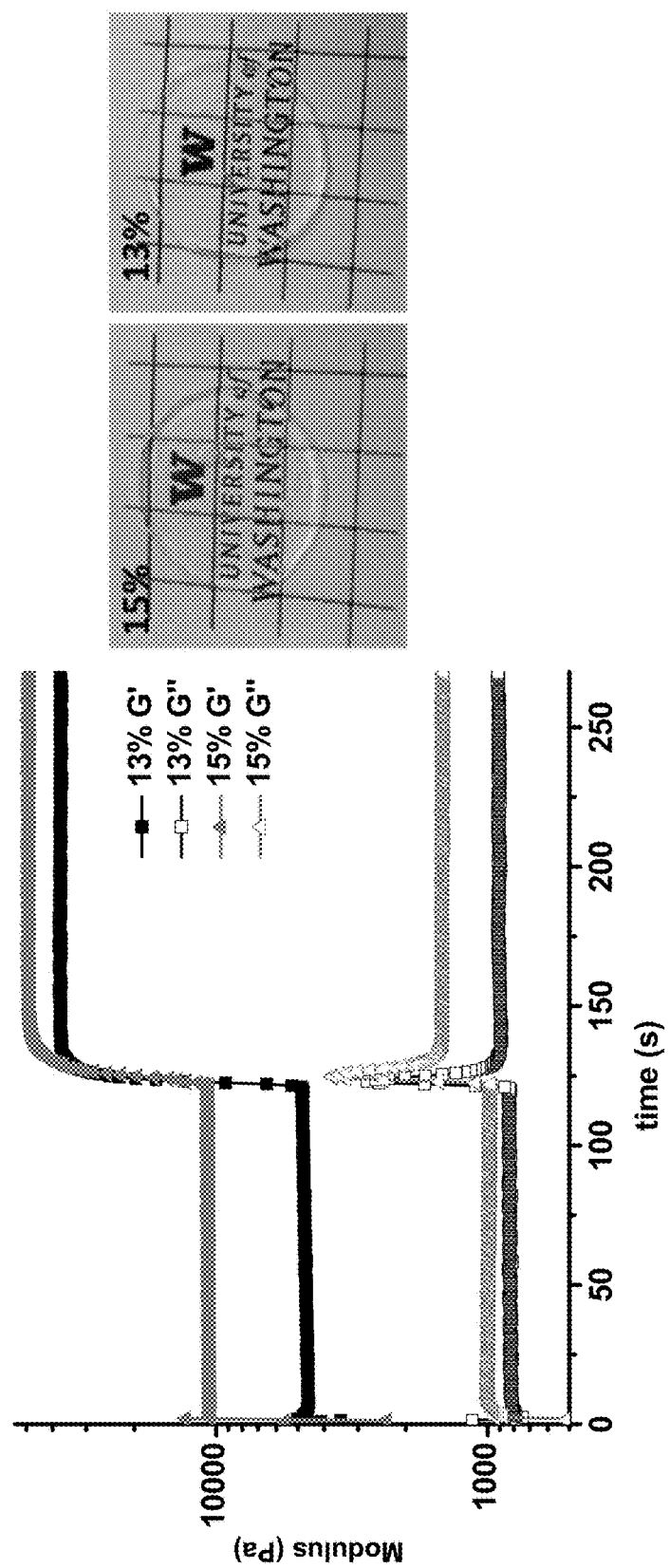
FIG. 10 is a plot of viscoelastic moduli with time for in situ UV curing (left) and images of UV cured transparent hydrogels of IPGE12.5-UDM (right), in accordance with an example embodiment.

The elastic modulus of the hydrogel was also dependent upon the UV exposure time and photo-initiator concentration (FIG. 9). When 1 wt % photoinitiator (relative to the polymer) was added to the polymer 6 hydrogel, the cross-linking reached its peak in 400 seconds to afford a modulus of 80 kPa. Continued UV exposure beyond this time did not change the G' modulus. Adjusting to shorter cure times can allow for reduced cross-link density and therefore G' moduli of 40 kPa and 68 kPa for 60 and 200 s cure times, respectively.

IPGEx-UDM Crosslinked Hydrogels.

To examine the influence of UV curing (chemical cross-linking) on the mechanical properties, the change in the viscoelastic property of the 13 wt % and 15 wt % hydrogels with in situ UV curing was monitored. The photoinitiator (2-hydroxy-2-methylpropiophenone; 1 wt % with respect to IPGE12.5-UDM) was added to the hydrogels of IPGE12.5-UDM, and the resulting hydrogel compositions were subjected to UV irradiation for 60 sec while the viscoelastic properties were measured at 1% of strain and at a frequency of 1 Hz. Appreciable increases in the storage moduli (G') were observed for both of the hydrogels after the UV treatment. Interestingly, the crosslinking was achieved within 15 sec after initiating the UV irradiation. A sharp change in storage moduli up to 15 sec and then a plateau indicated that the crosslinking reaction reached saturation within 15 sec (FIG. 6). Storage moduli (G') increased from 4.8 kPa to 37 kPa for 13 wt % and for 15 wt % from 10.6 kPa to 46 kPa, respectively. Another interesting feature of the hydrogels is that the transparency of the hydrogels was retained even after chemical crosslinking (FIG. 9).

Algae-Loaded Hydrogel Preparation

A hydrogel loaded with the alga *Chlamydomonas* was prepared by cooling a 15 wt % gel in an ice bath and adding a concentrated stock solution of the alga. After mixing, the viscous solution was allowed to warm to ambient temperature to generate a homogenous green gel. The algae-loaded gel was printed using a direct-write 3D printer (FIG. 9).

Preparation of Yeast-Loaded Crosslinked Hydrogel Structures

A pinch of yeast cells (SO992) were collected by a sterile wooden inoculation pick from a casted agar gel in YPD media. The cells were homogeneously mixed into 7 mL SC media and incubated at 30° C. under constant shaking at 225 rpm for 24 hours. After 24 hours, the thick precipitate was observed, indicating plenty of cells were grown. 100 uL of the solution were mixed with 1900 uL of SC media and OD at 600 nm for this diluted solution was measured to count the number of cells (OD of 0.1 corresponds to $10^6$ cells/mL).

Polymer (3 g) was dissolved in SCM Media (7.5 g) and cooled at 5° C. overnight. Three to four hours before printing, WT yeast cells (SO992) at $10^8$ cells/mL and photo radical generator 2-hydroxymethyl propiophenone (10 uL) was manually mixed into the gel and allowed to equilibrate at 5° C. until bubbles were removed. The solution was then transferred directly into a Nordson Optimum 10 cc fluid dispensing barrel equipped with a Metcal conical (210, 260, or 410 μm inner diameter) precision tip nozzle. Upon reaching room temperature, the hydrogels were used as a bio-ink for direct-write 3D printing. The extruded hydrogel compositions were photo-crosslinked by UV irradiation (365 nm at 3.4 mW/cm$^2$) for 3 minutes to provide cross-linked hydrogel structures.

Ethanol Production

A crosslinked hydrogel structure containing embedded yeast cells was immersed into 10 mL of SC media in a 50 mL centrifuge tube. Then Ar gas was bubbled through the SC media for 6 minutes to remove the dissolved air and also to eliminate the air of the centrifuge tube. Then the tube was immediately sealed and kept at 30° C. under constant shaking at 225 rpm for 48 hours. After 48 hours 500 uL of the SC media were filtered through 0.2 uM membrane and subjected to GC analysis for quantification of the ethanol, produced by the yeast cells embedded in the crosslinked hydrogel structure.

The invention claimed is:
1. A crosslinked hydrogel structure comprising:
a polymer of formula (I):

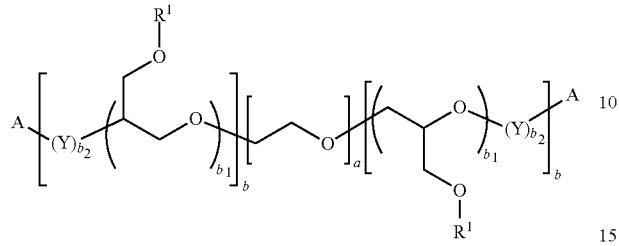

wherein
a is selected to provide a poly(ethylene glycol) block polymer with an $M_n$ of about 500 to about 50,000;
$R^1$ is $C_{1-12}$alkyl, $C_{1-12}$alkyl-OR or $C_{1-12}$alkyl-NR$_2$, wherein each R is independently hydrogen or $C_{1-12}$alkyl;
$(Y)_{b_2}$ is absent or a glycidyl ether derivative of the structure:

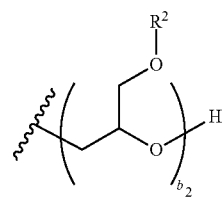

wherein $R^2$ is $C_{2-12}$alkenyl;

each $b_1$ and $b_2$ are independently selected to provide a random glycidyl ether derived copolymer with an $M_n$ about 100 to about 30,000; and A is hydrogen or a (meth)acrylate derivative of the structure:

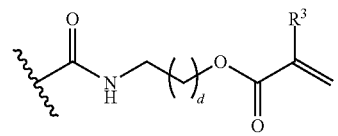

wherein
$R^3$ is hydrogen or methyl; and
d is 0, 1, 2, 3, 4, 5, 6, 7, 8, 9, 10, 11 or 12;
provided that
(a) when $(Y)_{b_2}$ is the glycidyl ether derivative, A is hydrogen; and
(b) when $(Y)b_2$ is absent, A is the (meth)acrylate derivative;
an aqueous media; and
a living cell;
wherein the polymer includes crosslinks derived from (i) the alkene groups of $R^2$ in different polymer chains cross-coupled to form covalent bonds, or (ii) the alkene groups of A in different polymer chains cross-coupled to form covalent bonds, and wherein the polymer crosslinks exclude thiol-ene bonds.

2. The crosslinked hydrogel of claim 1, wherein the polymer has the structure of Formula (II):

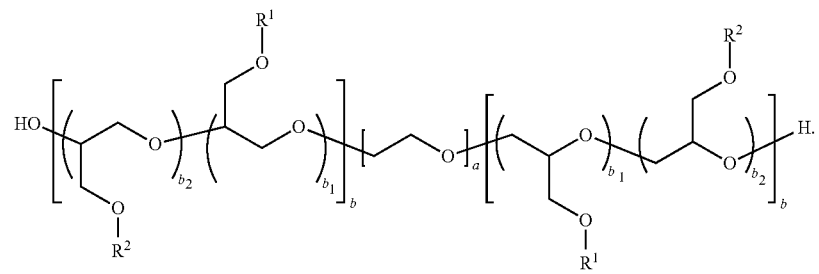

3. The crosslinked hydrogel of claim 2, wherein
$R^1$ is $C_{1-6}$alkyl; and
$R^2$ is $C_{2-6}$alkenyl.
4. The crosslinked hydrogel of claim 2, wherein the polymer has the structure of Formula (IIa):

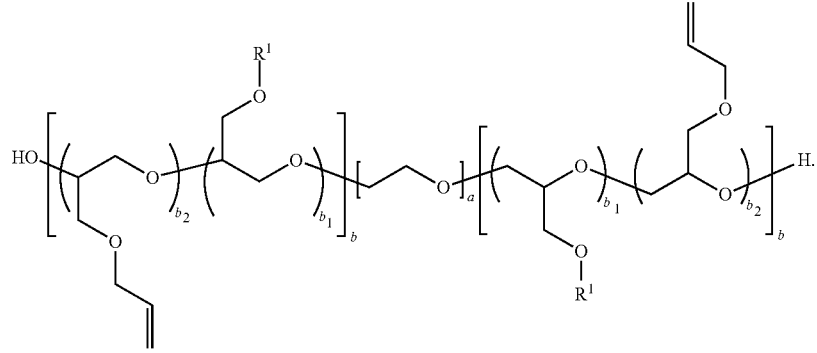

5. The crosslinked hydrogel of claim 2, wherein $R^1$ is $C_{1-6}$alkyl.

6. The crosslinked hydrogel of claim 2, wherein the polymer has the structure of Formula (IIb):

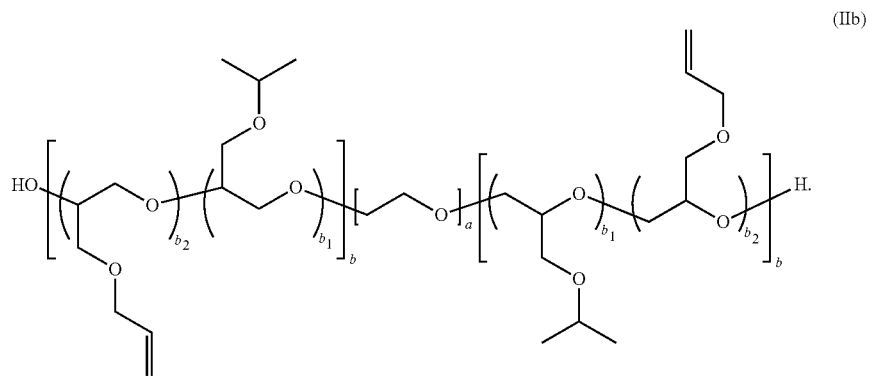

(IIb)

7. The crosslinked hydrogel of claim 2, wherein the polymer has the structure of Formula (IIc):

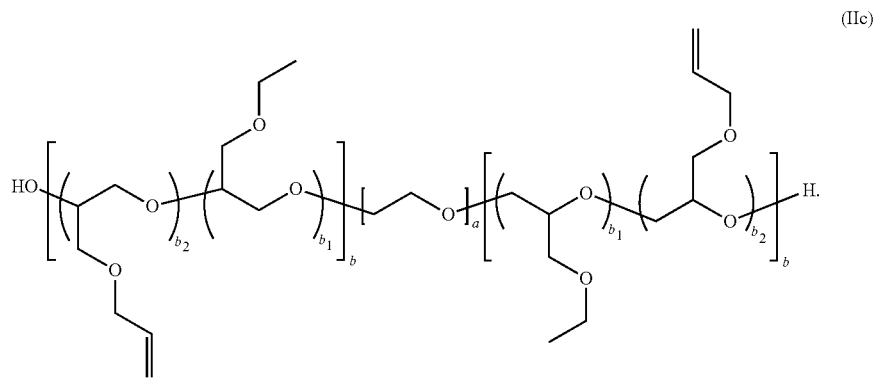

(IIc)

8. The crosslinked hydrogel of claim 1, wherein the polymer has the structure of Formula (III):

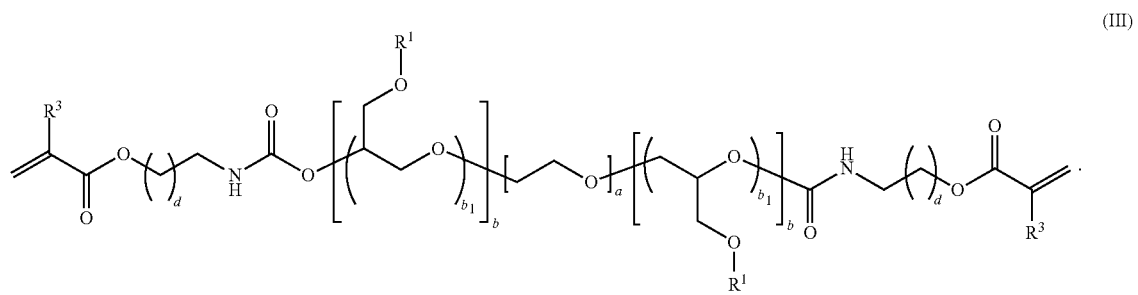

(III)

9. The crosslinked hydrogel of claim 8, wherein $R^1$ is $C_{1-6}$alkyl.

10. The crosslinked hydrogel of claim 8, wherein the polymer has the structure of Formula (IIIa):

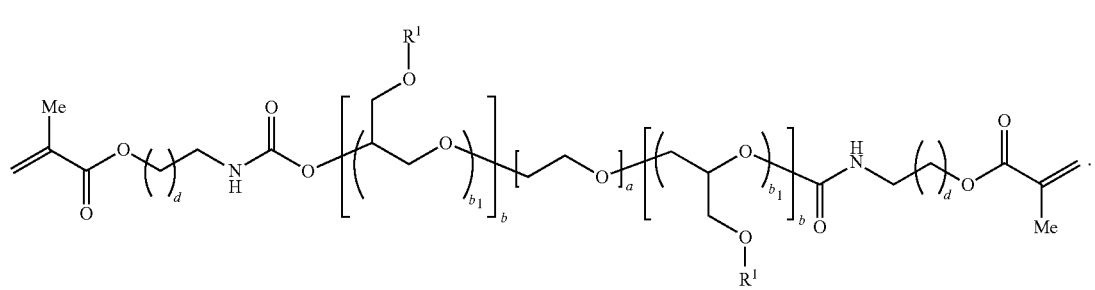

(IIIa)

11. The crosslinked hydrogel of claim 8, wherein the polymer has the structure of Formula (IIIb):

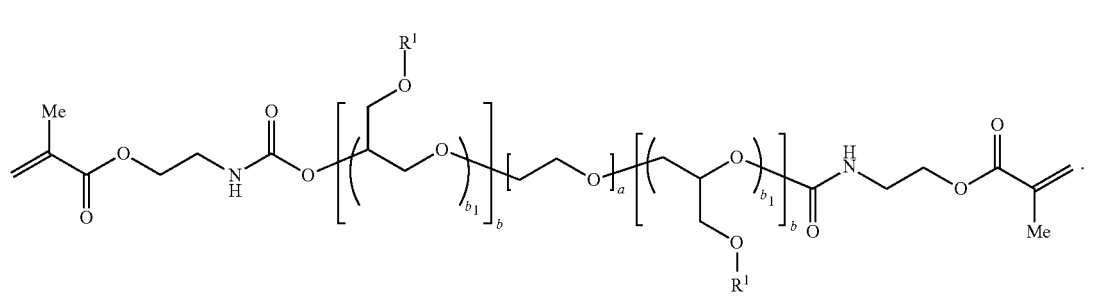

(IIIb)

12. The crosslinked hydrogel of claim 8, wherein the polymer has the structure of Formula (IIIc):

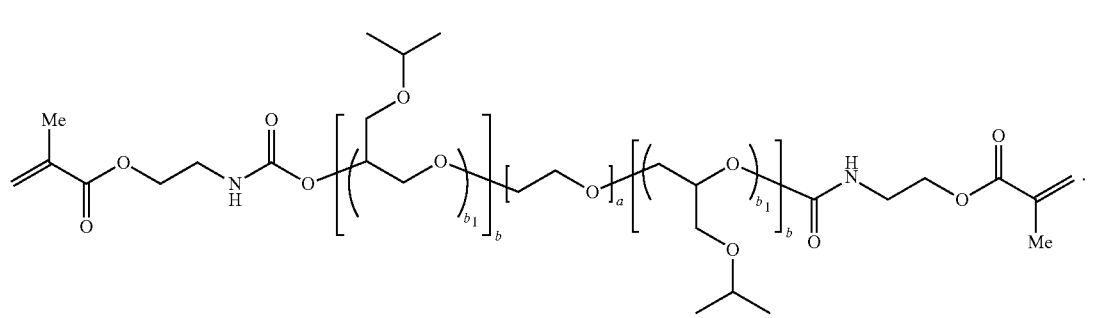

(IIIc)

13. A method for forming a crosslinked hydrogel structure of claim 1, the method comprising subjecting the polymer to UV light to initiate crosslinking between the alkene groups of $R^2$ in different polymer chains, or between the alkene groups of A in different polymer chains.

14. The method of claim 13, wherein the polymer is subjected to UV light in the presence of photoinitiator and a loading agent.

15. The method of claim 14, wherein the loading agent is a living cell.

16. A method for extrusion printing, the method comprising:

(a) obtaining a hydrogel composition comprising a polymer of formula (I):

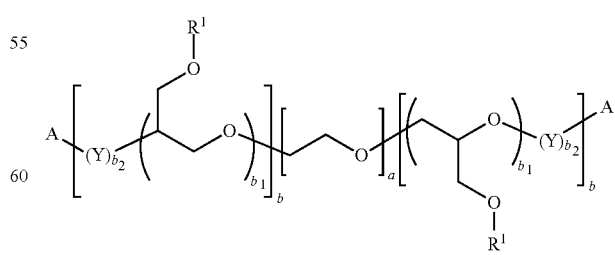

(I)

wherein a is selected to provide a poly(ethylene glycol) block polymer with an $M_n$ of about 500 to about 50,000;

$R^1$ is $C_{1-12}$alkyl, $C_{1-12}$alkyl-OR or $C_{1-12}$alkyl-NR$_2$, wherein each R is independently hydrogen or $C_{1-12}$alkyl;

$(Y)_{b2}$ is absent or a glycidyl ether derivative of the structure:

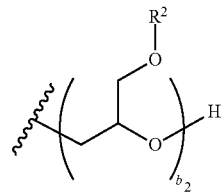

wherein $R^2$ is $C_{2-12}$alkenyl;

each $b_1$ and $b_2$ are independently selected to provide a random glycidyl ether derived copolymer with an $M_n$ about 100 to about 30,000; and A is hydrogen or a (meth)acrylate derivative of the structure:

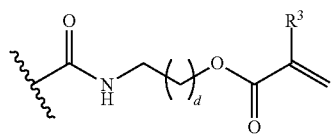

wherein $R^3$ is hydrogen or methyl; and d is 0, 1, 2, 3, 4, 5, 6, 7, 8, 9, 10, 11 or 12;

provided that (a) when $(Y)_{b2}$ is the glycidyl ether derivative, A is hydrogen; and (b) when (Y)b$_2$ is absent, A is the (meth)acrylate derivative, an aqueous media, a photoinitiator and living cells;

(b) extrusion printing the composition to provide an extruded hydrogel composition; and (c) subjecting the extruded hydrogel composition to UV light to initiate crosslinking between the alkene groups of $R^2$ in different polymer chains, or between the alkene groups of A in different polymer chains to form crosslinked hydrogel composition, and wherein the polymer crosslinks exclude thiol-ene bonds.

17. A method for performing a chemical reaction catalyzed by living cells, the method comprising:

(a) subjecting the crosslinked hydrogel structure of claim 1 to a reactant capable of undergoing chemical reaction; and (b) recovering the product of the chemical reaction.

* * * * *